US009789066B2

(12) United States Patent
Szymczak et al.

(10) Patent No.: US 9,789,066 B2
(45) Date of Patent: Oct. 17, 2017

(54) PROCESS FOR MAKING TABLET USING RADIOFREQUENCY AND LOSSY COATED PARTICLES

(71) Applicant: JOHNSON & JOHNSON CONSUMER INC., Skillman, NJ (US)

(72) Inventors: Christopher E. Szymczak, Marlton, NJ (US); Vipul Dave, Hillsborough, NJ (US); Gerard P. McNally, Berwyn, PA (US); David B. Cochran, Horsham, PA (US); Gregory Koll, Hillsborough, NJ (US); Stephen Ulrich, Cherry Hill, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

(21) Appl. No.: 14/592,176

(22) Filed: Jan. 8, 2015

(65) Prior Publication Data
US 2015/0196493 A1  Jul. 16, 2015

Related U.S. Application Data

(60) Provisional application No. 61/925,713, filed on Jan. 10, 2014.

(51) Int. Cl.
| | |
|---|---|
| *B01J 2/00* | (2006.01) |
| *B01J 2/18* | (2006.01) |
| *A61K 9/20* | (2006.01) |
| *A61K 31/137* | (2006.01) |
| *A61K 31/138* | (2006.01) |
| *A61K 31/167* | (2006.01) |
| *A61K 9/50* | (2006.01) |

(52) U.S. Cl.
CPC .......... *A61K 9/2095* (2013.01); *A61K 9/2081* (2013.01); *A61K 9/50* (2013.01); *A61K 31/137* (2013.01); *A61K 31/138* (2013.01); *A61K 31/167* (2013.01); *B01J 2/006* (2013.01); *B01J 2/18* (2013.01)

(58) Field of Classification Search
None
See application file for complete search history.

(56) References Cited

U.S. PATENT DOCUMENTS

| | | | |
|---|---|---|---|
| 2,183,053 A | 12/1939 | Taylor | |
| 2,887,437 A | 5/1959 | Klioze et al. | |
| 3,071,470 A | 1/1963 | Bishop | |
| 3,145,146 A * | 8/1964 | Lieberman | A61K 9/2018 424/465 |
| 3,586,066 A | 6/1971 | Brown | |
| 3,670,065 A | 6/1972 | Eriksson et al. | |
| 3,885,026 A | 5/1975 | Heinemann et al. | |
| 4,158,411 A | 6/1979 | Hall et al. | |
| 4,173,626 A | 11/1979 | Dempski et al. | |
| 4,230,693 A | 10/1980 | Izzo et al. | |
| 4,238,431 A | 12/1980 | Stuben et al. | |
| 4,260,596 A | 4/1981 | Mackles | |
| 4,268,238 A | 5/1981 | Marc | |
| 4,268,465 A | 5/1981 | Suh et al. | |
| 4,327,076 A | 4/1982 | Puglia et al. | |
| 4,396,564 A | 8/1983 | Stuben et al. | |
| 4,398,634 A | 8/1983 | McClosky | |
| 4,508,740 A | 4/1985 | McSweeney | |
| 4,526,525 A | 7/1985 | Oiso et al. | |
| 4,590,075 A | 5/1986 | Wei et al. | |
| 4,609,543 A | 9/1986 | Morris et al. | |
| 4,642,903 A | 2/1987 | Davies | |
| 4,684,534 A | 8/1987 | Valentine | |
| 4,758,439 A | 7/1988 | Godfrey | |
| 4,762,719 A | 8/1988 | Forester | |
| 4,777,050 A | 10/1988 | Vadino | |
| 4,824,681 A | 4/1989 | Schobel et al. | |
| 4,828,845 A | 5/1989 | Zamudio-Tena et al. | |
| 4,832,956 A | 5/1989 | Gergely et al. | |
| 4,851,226 A | 7/1989 | Julian et al. | |
| 4,857,331 A | 8/1989 | Shaw et al. | |
| 4,863,742 A | 9/1989 | Panoz et al. | |
| 4,906,478 A | 3/1990 | Valentine et al. | |
| 4,979,720 A | 12/1990 | Robinson | |
| 4,980,170 A | 12/1990 | Schneider et al. | |

(Continued)

FOREIGN PATENT DOCUMENTS

| | | |
|---|---|---|
| CN | 1119934 A | 4/1996 |
| CN | 1141589 A | 1/1997 |

(Continued)

OTHER PUBLICATIONS

Jones, P. L. et al, "Dielectric Drying", Drying Technology, 14(5), 1996, p. 1063-1098.
Guo, et al., Temperature and Moisture Dependent Dielectric Properties of Legume Flour Associated with Dielectric Heating, LWT Food Science and Technology 43, 2010, p. 193-201.
Katsuki, et al., Novel Energy-Saving Materials for Microwave Heating, Chem Mater. 2008, 20, p. 4803-4807.
Radio-Frequency Heating of Plastics, TechCommentary, vol. 4, No. 2, 1987, p. 1-4.
Jones, P. L., High Frequency Dielectric Heating in Paper Making, Drying Technology, 4(2), 1986, p. 217-244.
What is R.F. Heat Sealing?, Dielectric Sealing Service, Inc., 2007, p. 1-6.

(Continued)

*Primary Examiner* — Abigail Vanhorn

(57) ABSTRACT

In one aspect the present invention features process for making a tablet comprising at least one pharmaceutically active agent, said method comprising the step of applying radiofrequency energy to a powder blend to sinter said powder blend into said tablet, wherein said powder blend comprises lossy coated particles and said at least one pharmaceutically active agent, wherein said lossy coated particles comprises a substrate that is at least partially coated with a lossy coating comprising at least one activator, wherein said substrate has a Q value of greater than 100 and said activator has a Q value of less than 75.

25 Claims, No Drawings

(56) References Cited

U.S. PATENT DOCUMENTS

| | | | |
|---|---|---|---|
| 4,984,240 A | 1/1991 | Keren-Zvi et al. |
| 4,994,260 A | 2/1991 | Kallstrand et al. |
| 5,013,557 A | 5/1991 | Tai |
| 5,046,618 A | 9/1991 | Wood |
| 5,064,656 A | 11/1991 | Gergely et al. |
| 5,073,374 A | 12/1991 | McCarty |
| 5,075,114 A | 12/1991 | Roche |
| 5,082,436 A | 1/1992 | Choi et al. |
| 5,109,893 A | 5/1992 | Derby |
| 5,112,616 A | 5/1992 | McCarty |
| 5,126,151 A | 6/1992 | Bodor et al. |
| 5,134,260 A | 7/1992 | Piehler et al. |
| 5,139,407 A | 8/1992 | Kim et al. |
| 5,178,878 A | 1/1993 | Wehling et al. |
| 5,215,755 A | 6/1993 | Roche et al. |
| 5,223,264 A | 6/1993 | Wehling et al. |
| 5,262,171 A | 11/1993 | Login et al. |
| 5,275,822 A | 1/1994 | Valentine et al. |
| 5,286,497 A | 2/1994 | Hendrickson et al. |
| 5,304,055 A | 4/1994 | Van Lengerich et al. |
| 5,320,848 A | 6/1994 | Greyer et al. |
| 5,330,763 A | 7/1994 | Gole et al. |
| 5,464,632 A | 11/1995 | Cousin et al. |
| 5,489,436 A | 2/1996 | Hoy et al. |
| 5,501,858 A | 3/1996 | Fuisz |
| 5,501,861 A | 3/1996 | Makimo et al. |
| 5,503,846 A | 4/1996 | Wehling et al. |
| 5,558,880 A | 9/1996 | Gole et al. |
| 5,558,899 A | 9/1996 | Kuzee et al. |
| 5,560,963 A | 10/1996 | Tisack |
| 5,587,172 A | 12/1996 | Cherukuri et al. |
| 5,587,179 A | 12/1996 | Gergely et al. |
| 5,607,697 A | 3/1997 | Alkire et al. |
| 5,622,719 A | 4/1997 | Myers et al. |
| 5,631,023 A | 5/1997 | Kearney et al. |
| 5,635,210 A | 6/1997 | Allen, Jr. et al. |
| 5,648,093 A | 7/1997 | Gole et al. |
| 5,653,993 A | 8/1997 | Ghanta et al. |
| 5,662,849 A | 9/1997 | Bogne et al. |
| 5,672,364 A | 9/1997 | Kato et al. |
| 5,720,974 A | 2/1998 | Makino et al. |
| 5,814,339 A | 9/1998 | Prudhoe |
| 5,886,081 A | 3/1999 | Sternowski |
| 5,912,013 A | 6/1999 | Rudnic et al. |
| 5,939,091 A | 8/1999 | Eoga et al. |
| 5,997,905 A | 12/1999 | McTeigue et al. |
| 6,024,981 A | 2/2000 | Khankari et al. |
| 6,060,078 A | 5/2000 | Lee |
| 6,103,260 A | 8/2000 | Luber et al. |
| 6,224,905 B1 | 5/2001 | Lawrence et al. |
| 6,228,398 B1 | 5/2001 | Devane et al. |
| 6,258,381 B1 | 7/2001 | Luber et al. |
| 6,270,805 B1 | 8/2001 | Chen et al. |
| 6,277,409 B1 | 8/2001 | Luber et al. |
| 6,284,270 B1 | 9/2001 | Lagoviyer et al. |
| 6,287,826 B1 | 9/2001 | Murakami et al. |
| 6,316,026 B1 | 11/2001 | Tatara et al. |
| 6,322,819 B1 | 11/2001 | Barnside et al. |
| 6,328,994 B1 | 12/2001 | Shimizu et al. |
| 6,465,010 B1 | 10/2002 | Lagoviyer et al. |
| 6,499,984 B1 | 12/2002 | Ghebre-Sellassie et al. |
| 6,569,463 B2 | 5/2003 | Patel et al. |
| 6,589,554 B1 | 7/2003 | Mizumoto et al. |
| 6,612,826 B1 | 9/2003 | Bauer et al. |
| 6,649,888 B2 | 11/2003 | Ryan et al. |
| 6,753,009 B2 | 6/2004 | Luber et al. |
| 6,767,200 B2 | 7/2004 | Sowden et al. |
| 6,814,978 B2 | 11/2004 | Bunick et al. |
| 6,932,979 B2 | 8/2005 | Gergely |
| 7,070,825 B2 | 7/2006 | Ndife et al. |
| 7,132,072 B2 | 11/2006 | Ozeki et al. |
| 7,157,100 B2 | 1/2007 | Doshi et al. |
| 7,625,622 B2 | 12/2009 | Teckoe et al. |
| 8,127,516 B2 | 3/2012 | Lee et al. |
| 8,313,768 B2 | 11/2012 | Kriksunov et al. |
| 8,343,533 B2 | 1/2013 | Chen et al. |
| 8,784,781 B2 | 7/2014 | Koll et al. |
| 8,807,979 B2 | 8/2014 | Sowden et al. |
| 8,858,210 B2 | 10/2014 | Szymczak et al. |
| 8,865,204 B2 | 10/2014 | Koll et al. |
| 8,871,263 B2 * | 10/2014 | Bunick ............... A61K 9/0056 424/464 |
| 2001/0033831 A1 | 10/2001 | Chow et al. |
| 2002/0012701 A1 | 1/2002 | Kolter et al. |
| 2002/0018800 A1 | 2/2002 | Pinney et al. |
| 2002/0079121 A1 | 6/2002 | Ryan et al. |
| 2002/0122822 A1 | 9/2002 | Bunick et al. |
| 2003/0021842 A1 | 1/2003 | Lagoviyer et al. |
| 2003/0068373 A1 | 4/2003 | Luber et al. |
| 2003/0114527 A1* | 6/2003 | Karnachi ............... A61K 31/196 514/567 |
| 2003/0161879 A1 | 8/2003 | Ohmori et al. |
| 2003/0175339 A1 | 9/2003 | Bunick et al. |
| 2003/0194442 A1 | 10/2003 | Guivarch et al. |
| 2003/0224044 A1 | 12/2003 | Weibel |
| 2003/0228368 A1 | 12/2003 | Wynn et al. |
| 2004/0115305 A1 | 6/2004 | Andersen et al. |
| 2004/0137057 A1 | 7/2004 | Sowden et al. |
| 2004/0156902 A1 | 8/2004 | Lee et al. |
| 2004/0191499 A1 | 9/2004 | Hallett et al. |
| 2005/0019407 A1 | 1/2005 | Sowden et al. |
| 2005/0138899 A1 | 6/2005 | Draisey et al. |
| 2005/0142188 A1 | 6/2005 | Gilis et al. |
| 2005/0186274 A1 | 8/2005 | Kohlrausch |
| 2006/0034927 A1 | 2/2006 | Casadevall et al. |
| 2006/0134195 A1 | 6/2006 | Fu et al. |
| 2007/0071806 A1 | 3/2007 | McCarty |
| 2007/0184111 A1 | 8/2007 | Harris et al. |
| 2007/0196477 A1 | 8/2007 | Witham et al. |
| 2007/0281009 A1 | 12/2007 | Kamisono et al. |
| 2008/0286340 A1 | 11/2008 | Andersson et al. |
| 2009/0060983 A1 | 3/2009 | Bunick et al. |
| 2009/0092672 A1 | 4/2009 | Venkatesh et al. |
| 2009/0110716 A1 | 4/2009 | Bunick et al. |
| 2009/0110717 A1 | 4/2009 | Singh et al. |
| 2009/0311320 A1 | 12/2009 | Oury et al. |
| 2010/0016348 A1 | 1/2010 | Bunick et al. |
| 2010/0016451 A1 | 1/2010 | Bunick et al. |
| 2010/0021507 A1 | 1/2010 | Bunick et al. |
| 2010/0034891 A1* | 2/2010 | Okochi ............... A61K 9/1635 424/490 |
| 2010/0278930 A1* | 11/2010 | Okumura ............... A61K 9/0056 424/499 |
| 2011/0068511 A1 | 3/2011 | Sowden et al. |
| 2011/0070170 A1 | 3/2011 | Koll et al. |
| 2011/0070286 A1 | 3/2011 | Hugerth et al. |
| 2011/0070301 A1 | 3/2011 | Luber et al. |
| 2011/0071184 A1 | 3/2011 | Bunick et al. |
| 2011/0071185 A1* | 3/2011 | Bunick ............... A61K 9/0056 514/290 |
| 2011/0318411 A1 | 12/2011 | Luber et al. |
| 2011/0319441 A1 | 12/2011 | Szymczak et al. |
| 2011/0319492 A1* | 12/2011 | Luber ............... A61K 9/0056 514/570 |
| 2012/0022170 A1* | 1/2012 | Bunick ............... A61K 9/0056 514/777 |
| 2013/0292884 A1 | 11/2013 | Anderson et al. |
| 2013/0295174 A1 | 11/2013 | Sowden et al. |
| 2013/0295175 A1 | 11/2013 | Chen et al. |
| 2013/0295211 A1 | 11/2013 | Stuhl et al. |

FOREIGN PATENT DOCUMENTS

| | | |
|---|---|---|
| CN | 1498080 A | 5/2004 |
| CN | 1578724 A | 2/2005 |
| CN | 1805735 A | 7/2006 |
| CN | 101052373 A | 10/2007 |
| EP | 0 070127 | 1/1983 |
| EP | 0192460 B1 | 8/1986 |
| EP | 0 416791 A2 | 3/1991 |
| EP | 0829341 A2 | 3/1998 |
| EP | 1974724 | 10/2008 |
| EP | 20308511 | 12/2012 |

(56) References Cited

FOREIGN PATENT DOCUMENTS

| | | |
|---|---|---|
| GB | 772 315 | 4/1957 |
| GB | 1 097207 | 12/1967 |
| GB | 1538280 A | 1/1979 |
| JP | 59067006 A | 4/1984 |
| JP | 62/205009 A | 3/1986 |
| JP | 649482 | 6/1994 |
| JP | 0649482 B | 6/1994 |
| JP | 1999033084 A | 2/1999 |
| JP | 2010531350 | 9/2010 |
| RU | 2082436 C | 6/1997 |
| RU | 2233854 C | 8/2004 |
| SU | 862816 A | 9/1981 |
| SU | 925673 A | 5/1982 |
| SU | 1632629 A | 3/1991 |
| WO | WO 91/12881 | 9/1991 |
| WO | WO 92/04920 A | 4/1992 |
| WO | WO 92/06679 | 4/1992 |
| WO | WO 93/13758 A1 | 7/1993 |
| WO | WO 94/06416 | 3/1994 |
| WO | WO 95/09044 A1 | 4/1995 |
| WO | WO 97/38679 A2 | 10/1997 |
| WO | WO 98/32426 | 7/1998 |
| WO | WO 99/17771 | 4/1999 |
| WO | WO 99/44580 | 9/1999 |
| WO | WO 00/04281 | 1/2000 |
| WO | WO 02/47607 | 6/2002 |
| WO | WO 03/059327 A1 | 7/2003 |
| WO | WO 03/061399 A1 | 7/2003 |
| WO | WO 03/101431 A1 | 12/2003 |
| WO | WO 04/000197 A2 | 12/2003 |
| WO | WO 2004/046296 A1 | 6/2004 |
| WO | WO 2004/100857 A2 | 11/2004 |
| WO | WO 2004/110413 A | 12/2004 |
| WO | WO 2006/018074 A1 | 2/2006 |
| WO | WO 2006/127618 | 11/2006 |
| WO | WO 2007/042153 | 4/2007 |
| WO | WO 2007/104574 A2 | 9/2007 |
| WO | WO 2007/125545 A2 | 11/2007 |
| WO | WO 2007/141328 | 12/2007 |
| WO | WO 2008/005318 A2 | 1/2008 |
| WO | WO 2008/015221 A2 | 2/2008 |
| WO | WO 2009/022670 A | 2/2009 |
| WO | WO 2009/032655 | 3/2009 |
| WO | WO 2009/037319 A2 | 3/2009 |
| WO | WO 2009/080022 A1 | 7/2009 |
| WO | WO 2010/058218 A1 | 5/2010 |
| WO | WO 2012/039788 A1 | 3/2012 |
| ZA | 8704899 | 3/1988 |

OTHER PUBLICATIONS

Broadband RF Survey Instruments, ETS•LINDGREN Haladay EMF Measurement, 2002, p. 1-2.
Lamp IR Infrared Heaters: Infrared Lamps for Controlled Concentrated Heating, Research Inc., p. 1-20., Sep. 20, 2010.
Callebaut, Power Quality & Utilisation Guide, Section 7: Energy Efficiency, Mar. 2007, www.leonardo-energy.org, p. 1-9.
Shukla, et al., Mouth Dissolving Tablets I: An Overview of Formulation Technology, Sci Pharm 2009, 76: p. 309-326.
Lieberman, Herbert A. et al., "Pharmaceutical Dosage Forms—Tablets", vol. 2, $2^{nd}$ Ed. pp. 213-217; 327-329, Marcel Dekker, Inc., 1990, New York and Basel.
Lachman, Leon et al., "The Theory and Practice of Industrial Pharmacy", $3^{rd}$ Ed., Chapter 11, pp. 293-345,Lea & Febiger, 1986, Philadelphia.
McConville, J. et al., "Erosion characteristics of an erodible tablet incorporated in a time-delayed capsule device," Drug Development and Industrial Pharmacy, vol. 31, No. 1, 2005, pp. 79-89, XP008108019.
USP 23 (1995) 1216, Tablet Friability, p. 1981.
USP 24, 2000 Version, Acetaminophen, pp. 19-20 and Ibuprofen, p. 856 (1999).
USP 30-NF25, Disintegration, pp. 276-277, 2007.
USP 33—U.S. Pharmacopeia, General Chapter 701—Disintegration, 2008.
Orally Disintegrating Tablets, draft Food and Drug Administration Guidance, Apr. 2007.
Heng, Paul Wan Sia, Chem Pharm Bull, 47 (5) 633-638 (1999).
Heng, P., et al., Melt Processes for Oral Solid Dosage Forms, Encyclopedia of Pharmaceutical Technology, vol. 4, Jan. 2, 2007, pp. 2257-2261.
Koral, Tony, Radio Frequency Heating and Post-Baking, Biscuit World, Issue 4, vol. 7, Nov. 2004.
Dielectric Heating with Microwave Energy, Püschner MikrowellenEnergietechnik, pp. 1-4, Jun. 2007.
Amin, Avani F., Emerging Treands in the Development of Orally Disintegrating Tablet Technology, Pharmainfo.net, vol. 4, Issue 1, Jan. 26, 2006; pp. 1-30.
Matthes, R.; "Chapter 49" from website: http://www.ilo.org/safework_bookshelf/english?content&nd=857170571; made available online Oct. 12, 2004.
Google page showing the availability date of web reference U; provided Mar. 15, 2011.
Rambali, B., et al., International Journal of Pharmaceutics 220 (2001), pp. 129-140.
Radio Frequency Company, Microwave, (Feb. 19, 2004), pp. 1-2.
Maltodextrin (Maltrin M580), Apr. 20, 2000, (PFormulate Excipients).
Int'l. Search Report for Application No. PCT/US2008/081496, dated Jul. 15, 2009.
Int'l. Search Report for Application No. PCT/US2008/74375, dated Nov. 17, 2008.
Int'l. Search Report for Application No. PCT/US2010/049909 dated Dec. 3, 2010.
Int'l. Search Report for Application No. PCT/US2010/049915 dated Mar. 25, 2011.
Int'l. Search Report for Application No. PCT/US2010/049925 dated Dec. 8, 2010.
Int'l. Search Report for Application No. PCT/US2010/049931 dated Jan. 7, 2011.
Search Report for Application No. PCT/US2010/049933 dated Feb. 15, 2011.
Int'l. Search Report for Application No. PCT/US2010/049964 dated Dec. 30, 2010.
Int'l. Search Report for Application No. PCT/US2010/049971 dated Jan. 7, 2011.
Int'l. Search Report for Application No. PCT/US2011/029155 dated Jun. 28, 2011.
Int'l. Search Report for Application No. PCT/US2011/029158 dated Jun. 28, 2011.
Int'l. Search Report for Application No. PCT/US2011/029161 dated Jun. 28, 2011.
Int'l. Search Report for Application No. PCT/US2010/049974 dated Mar. 5, 2013.
Int'l. Search Report for Application No. PCT/US2013/039040 dated Nov. 7, 2013.
International Search Report dated Aug. 20, 2013 for Application No. PCT/US2013/039045.
International Search Report dated Aug. 21, 2013 for Application No. PCT/US2013/039061.
Int'l. Search Report for Application No. PCT/US2013/039047 dated Jun. 8, 2013.
European Search Report dated Aug. 1, 2013 for Application No. EP08798740.
U.S. Appl. No. 11/847,444, filed Aug. 30, 2007, Bunick et al.
U.S. Appl. No. 12/570,046, filed Sep. 30, 2009, Bunick et al.
U.S. Appl. No. 60/983,973, filed Oct. 31, 2007, Bunick et al.
U.S. Appl. No. 12/260,151, filed Oct. 29, 2008, Bunick et al.
U.S. Appl. No. 12/566,078, filed Sep. 24, 2009, Bunick et al.
U.S. Appl. No. 12/566,096, filed Sep. 24, 2009, Bunick et al.
U.S. Appl. No. 61/245,315, filed Sep. 24, 2009, Sowden et al.
U.S. Appl. No. 61/255,582, filed Oct. 28, 2009, Sowden et al.
U.S. Appl. No. 61/314,629, filed Mar. 17, 2010, Kriksunov et al.
U.S. Appl. No. 61/358,167, filed Jun. 24, 2010, Luber et al.
U.S. Appl. No. 12/887,544, filed Sep. 22, 2010, Bunick et al.
U.S. Appl. No. 12/887,552, filed Sep. 22, 2010, Bunick et al.

(56) References Cited

OTHER PUBLICATIONS

U.S. Appl. No. 12/887,560, filed Sep. 22, 2010, Kriksunov et al.
U.S. Appl. No. 12/887,564, filed Sep. 22, 2010, Luber et al.
U.S. Appl. No. 12/887,569, filed Sep. 22, 2010, Sowden et al.
U.S. Appl. No. 12/887,575, filed Sep. 22, 2010, Koll et al.
U.S. Appl. No. 12/887,582, filed Sep. 22, 2010, Luber et al.
U.S. Appl. No. 12/887,593, filed Sep. 22, 2010, Hugerth et al.
U.S. Appl. No. 13/052,316, filed Mar. 21, 2011, Luber et al.
U.S. Appl. No. 13/052,219, filed Mar. 21, 2011, Sowden et al.
U.S. Appl. No. 13/052,200, filed Mar. 21, 2011, Luber et al.
U.S. Appl. No. 13/246,884, filed Sep. 28, 2011, Sowdent et al.
U.S. Appl. No. 13/718,357, filed Dec. 18, 2012, Koll et al.
U.S. Appl. No. 14/455,126, filed Aug. 8, 2014, Luber et al.
U.S. Appl. No. 61/640,910, filed May 1, 2012, Chen et al.
U.S. Appl. No. 61/704,767, filed Sep. 24, 2012, Chen et al.
U.S. Appl. No. 61/704,773, filed Sep. 24, 2012, Anderson et al.
U.S. Appl. No. 61/704,780, filed Sep. 24, 2012, Stuhl et al.
U.S. Appl. No. 13/803,527, filed Mar. 14, 2013, Chen et al.
U.S. Appl. No. 13/804,109, filed Mar. 14, 2013, Sowden et al.
U.S. Appl. No. 13/804,229, filed Mar. 14, 2013, Anderson et al.
U.S. Appl. No. 13/804,410, filed Mar. 14, 2013, Stuhl et al.
U.S. Appl. No. 61/925,713, filed Jan. 10, 2014, Szymczak et al.
U.S. Appl. No. 14/592,176, filed Jan. 8, 2015, Szymczak et al.
International search report for application PCT/US2015/010647 dated Mar. 18, 2015.

* cited by examiner

PROCESS FOR MAKING TABLET USING RADIOFREQUENCY AND LOSSY COATED PARTICLES

CROSS REFERENCE TO RELATED APPLICATIONS

This application claims priority of the benefits of U.S. Provisional Application Ser. No. 61/925,713, filed Jan. 10, 2014. The complete disclosure of the aforementioned related U.S. patent application is hereby incorporated by reference for all purposes.

BACKGROUND OF THE INVENTION

Pharmaceuticals intended for oral administration are typically provided in tablet form. Tablets can be swallowed whole, chewed in the mouth, or disintegrated in the oral cavity. Soft tablets that either are chewed or dissolve in the mouth are often employed in the administration of pharmaceuticals where it is impractical to provide a tablet for swallowing whole. With chewable tablets, the act of chewing helps to break up the tablet particles as the tablet disintegrates and may increase the rate of absorption by the digestive tract. Soft tablets are also advantageous where it is desirable to make a pharmaceutically active agent available topically in the mouth or throat for both local effects and/or systemic absorption. Soft tablets are also utilized to improve drug administration in pediatric and geriatric patients. Soft tablets designed to disintegrate in the mouth prior to swallowing are particularly useful for improving compliance of pediatric patients.

Generally, soft tablets are made by compaction of a blend of powdered ingredients and typically include a pharmaceutically active agent, flavoring, and/or binders. The powder blend is typically fed into the cavity of a die of a tablet press and a tablet is formed by applying pressure. Hardness of the resulting tablet is a direct function of the compaction pressure employed and the compatibility of the ingredients in the formulation. A softer tablet, having an easier bite-through, may be prepared by employing reduced compaction pressures. The resulting tablet is softer, but also more fragile, brittle, and easily chipped and disadvantageously can involve complex and costly processing steps. Examples of soft tablets designed to disintegrate in the mouth without chewing are disclosed in U.S. Pat. Nos. 5,464,632, 5,223,264, 5,178,878, 6,589,554, and 6,224,905.

There is a need for aesthetically pleasing chewable and orally disintegrating tablets that utilize commercially efficient manufacturing methods. Orally disintegrating tablets can be prepared by compression (see, e.g., U.S. Pat. Nos. 5,223,264 and 5,178,878), but these tablets can have a high density and thus can take up to 20 to 30 seconds to fully disintegrate in the mouth. Lyophilized orally disintegrating tablets (see, e.g., U.S. Pat. Nos. 6,509,040, 5,976,577, 5,738,875, and 5,631,023) tend to be less dense and, thus, faster disintegrating. However, these tablets require a long time to make a tablet, and the process of lyophilization of the tablet formulation directly in the unit dose blister package renders a dosage form that is shaped on only one face. The amount of drug loading in this lyophilization process is also limited.

The present invention relates to a new process for manufacturing tablets, such as orally disintegrating tablets ("ODTs") utilizing lossy coated particles where the lossy coating comprises an activator that is used to sinter to particles to form the tablet. As this process concentrates the activator on the surface of the particle, the amount of activator added to the tablet can be reduced and the sintering of particles can be improved, resulting in tablet properties such as improved friability, better mouthfeel, faster disintegration, higher pharmaceutically active agent loading, and/or shorter manufacturing time as compared to tablets those made by other similar processes such US Patent Application Nos. 2009/0060983, 2011/0071184, and 2013/0295175 as set forth herein.

SUMMARY OF THE INVENTION

In one aspect, the present invention features a process for making a tablet comprising at least one pharmaceutically active agent, said method comprising the step of applying radiofrequency energy to a powder blend to sinter said powder blend into said tablet, wherein said powder blend comprises lossy coated particles and said at least one pharmaceutically active agent, wherein said lossy coated particles comprises a substrate that is at least partially coated with a lossy coating comprising at least one activator, wherein said substrate has a Q value of greater than 100 and said activator has a Q value of less than 75.

In another aspect, the present invention features a process for making a tablet comprising at least one pharmaceutically active agent, said method comprising the step of applying radiofrequency energy to a powder blend to sinter said powder blend into said tablet, wherein said powder blend comprises lossy coated particles and said at least one pharmaceutically active agent, wherein said lossy coated particles comprise of a substrate that is at least partially coated with a lossy coating comprising at least one activator, wherein the Q value of the activator is less than half the Q value of the substrate.

In another aspect, the sintered tablet comprising lossy coated particles and at least one pharmaceutically active agent, wherein said lossy coated particles comprise a substrate that is at least partially coated with a lossy coating comprising at least one activator, wherein said substrate has a Q value of greater than 100 and said activator has a Q value of less than 75.

In another aspect, the sintered tablet comprising lossy coated particles and at least one pharmaceutically active agent, wherein said lossy coated particles comprise a substrate that is at least partially coated with a lossy coating comprising at least one activator, wherein the Q value of the activator is less than half the Q value of the substrate.

Other features and advantages of the present invention will be apparent from the detailed description of the invention and claims.

DETAILED DESCRIPTION OF THE INVENTION

It is believed that one skilled in the art can, based upon the description herein, utilize the present invention to its fullest extent. The following specific embodiments can be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. As used herein, all percentages are by weight unless otherwise specified.

As discussed above, in one aspect, the present invention features:

Powder Blend

In one embodiment, the tablet is manufactured by applying radiofrequency energy to a powder blend containing at least one pharmaceutically active agent (as discussed herein), lossy coated particles (as discussed herein), and optionally other suitable excipients. In one embodiment, the said at least one pharmaceutically active agent is contained within separate particles within the powder blend. In one embodiment, the said at least one pharmaceutically active agent is contained within the lossy coated particles.

In one embodiment, the powder blend/tablet comprises at least 20%, by weight, of said lossy coated particles, such as at least 50%, by weight, such as at least 70%, by weight.

Examples of suitable excipients include, but are not limited to, fillers, water scavengers, glidants, sweeteners, flavor and aromatics, antioxidants, preservatives, texture enhancers, colorants, and mixtures thereof. One or more of the above ingredients may be present on the same particle of the powder blend.

Examples of fillers include but not limited to starches, sugar alcohols, bulk sweeteners, polyols, polymers and plasticizers.

In one embodiment, the powder blend/tablet comprises a water scavenger such as a starch and/or a silica. A benefit of the presence of a water scavenger in the powder blend is that it can act to retain water within the powder blend following the application of radiofrequency energy. Examples of starches include, but are not limited to, vegetable starches such as pea and corn starches and modified starches (such as pregelantized, acid modified, or dextrinized starches) or derivatized starches (such as cross linked, acetylated, and hydroxy alkyl starches). Examples of silicas include fumed silicas such as Syloid® FP silicas from Grace (Columbia, Md., USA), clays such as bentonite, veegum, and neusilin. In one embodiment, the powder blend/tablet comprises from about 0.1-10%, by weight, of said water scavenger, such as from about 0.1-2%, by weight.

Examples of glidants include, but are not limited to, colloidal silicon dioxide.

Examples of sweeteners for the present inventions include, but are not limited to high intensity sweeteners such as synthetic or natural sugars; artificial sweeteners such as saccharin, sodium saccharin, aspartame, acesulfame, thaumatin, glycyrrhizin, sucralose, dihydrochalcone, alitame, miraculin, monellin, and stevside.

Examples of flavors and aromatics include, but are not limited to, essential oils including distillations, solvent extractions, or cold expressions of chopped flowers, leaves, peel or pulped whole fruit containing mixtures of alcohols, esters, aldehydes and lactones; essences including either diluted solutions of essential oils, or mixtures of synthetic chemicals blended to match the natural flavor of the fruit (e.g., strawberry, raspberry and black currant); artificial and natural flavors of brews and liquors, e.g., cognac, whisky, rum, gin, sherry, port, and wine; tobacco, coffee, tea, cocoa, and mint; fruit juices including expelled juice from washed, scrubbed fruits such as lemon, orange, and lime; spear mint, pepper mint, wintergreen, cinnamon, cacoe/cocoa, vanilla, liquorice, menthol, eucalyptus, aniseeds nuts (e.g., peanuts, coconuts, hazelnuts, chestnuts, walnuts, cola nuts), almonds, raisins; and powder, flour, or vegetable material parts including tobacco plant parts, e.g., genus *Nicotiana*, in amounts not contributing significantly to the level of nicotine, and ginger.

Examples of antioxidants include, but are not limited to, tocopherols, ascorbic acid, sodium pyrosulfite, butylhydroxytoluene, butylated hydroxyanisole, edetic acid, and edetate salts, and mixtures thereof.

Examples of preservatives include, but are not limited to, citric acid, tartaric acid, lactic acid, malic acid, acetic acid, benzoic acid, and sorbic acid, and mixtures thereof.

Examples of texture enhancers include, but are not limited to, pectin, polyethylene oxide, and carrageenan, and mixtures thereof. In one embodiment, texture enhancers are used at levels of from about 0.1% to about 10% percent by weight.

In one embodiment of the invention, the powder blend has an average particle size of less than 500 microns, such as from about 50 microns to about 500 microns, such as from about 50 microns and 300 microns.

As used herein, what is meant by "substantially free" is less than 5%, such as less than 1%, such as less than 0.1%, such as completely free (e.g., 0%).

In one embodiment, the powder blend/tablet is substantially free of super disintegrants. Super disintegrants include croscarmellose sodium, sodium starch glycolate, and cross-linked povidone. A composition substantially free of super-disintegrants is advantageous for enhancing mouth-feel and tablet stability due to reduced water absorbance.

In one embodiment the powder blend is substantially free of lubricants such as magnesium stearate or stearic acid. Avoidance of tablet lubricants is advantageous since these materials are known to slow dissolution and have a negative impact on taste such as imparting a bitter aftertaste.

Lossy Coated Particles

The present invention features a powder blend/tablet comprising lossy coated particles comprising a substrate that is at least partially coated with a lossy coating comprising at least one activator. Such particles allow for controlled heating of the powder blend for the manufacture of the sintered tablet.

Methods of manufacturing such lossy coated particles include, but are not limited to, top spray coating, top spray granulation, wurster coating, rotor coating, high shear granulation, spray drying, spray congealing, hot melt extrusion, microencapsulation, spinning disk coating, and extrusion/spheronization. In one embodiment, the coating material is dissolved into solution and sprayed onto the substrate. In another embodiment, the coating is blended with the substrate and water is added to the blend, utilizing processes such as high shear granulation or spray drying. In one embodiment, the coating solution is aqueous optionally containing other solvents.

In one embodiment, the activator is a cellulosic polymer. Suitable cellulosic polymers include but are not limited to, hydroxypropylcellulose, hydroxyethylcellulose, carboxymethylcellulose, methylcellulose, hypromellose, and mixtures thereof. Other suitable activators include polysaccharides and proteins such as starches, modified starches, gelling starches, and hydrocolloids; including but not limited to guar gum, carrageenan, maltodextrin, inulin, and, polyvinyl pyrrolidone. Still other suitable activators include acrylic polymers such as but not limited to: methacrylates such as polymethylmethacrylates; polyvinyls such as polyvinyl alcohols, polyvinylpyrrolidones, polyvinyl caprolactams, and polyvinyl acetates; and copolymers thereof such as copolymers of ethyl acrylate and methyl methacrylates, and polycaprolactones. In one embodiment, the weight average molecular weight of the activator is less than 360,000 daltons, such as less than 180,000 daltons.

In one embodiment, the substrate (e.g., is the form of a particle) is comprised of materials selected from starches, sugars, sugar alcohols, dicalcium phosphate, and microcrystalline cellulose. Suitable sugars include but are not limited to sucrose, mannose, maltose, lactose, fructose, dextrose, and dextrose monohydrate. Suitable sugar alcohols include but are not limited to erythritol, sorbitol, xylitol, mannitol, and maltitol. In one embodiment, the substrate comprises the pharmaceutically active agent. In one embodiment, the substrate is coated with first coating prior to the addition of the lossy coating.

In one embodiment, the average particle size of the lossy coated particle is from about 50 to about 500 microns, such as from about 50 to about 400 microns, such as from about 50 to about 300 microns.

The lossy coated particle is at least partially coated with the coating. What is meant by at least partially coated is that at least 25% of the total surface area is covered with the coating, such as at least 50%, such as at least 75%, such as 100%. In one embodiment, the amount of activator(s) in the lossy coated particles is at least about 0.25%, by weight, of the lossy coated particles, such as at least about 0.4%, by weight. In one embodiment, the amount of activator(s) in the lossy coated particles is from about 0.1% to about 20%, by weight, of the lossy coated particles, such as from about 0.1% to about 10%, by weight, of the lossy coated particles, such as from about 0.1% to about 2%, by weight, of the lossy coated particles.

In one embodiment, the lossy coated particle contains water. In this embodiment, the lossy coated particle comprises at least 0.1 percent, by weight, water, such as at least 0.3 percent, by weight, water, such as at least 0.5 percent, by weight, water when measured using loss on drying at 105° C. until the weight of the lossy coated particles has stabilized. In one embodiment, the lossy coated particle retains water when measured by loss on drying prior to sintering, such as moisture content of at least 0.1 percent by weight, such as from about 0.1 to about 3 percent, such as from about 0.5 to about 2 percent, by weight.

In one embodiment the coating comprises more than one activator, such as two activators. In one embodiment, the coating comprises two polymers.

In one embodiment, the coating comprises a plasticizer. Suitable plasticizers for include, but not be limited to: polyethylene glycol; propylene glycol; glycerin; sorbitol; triethyl citrate; tributyl citrate; dibutyl sebecate; vegetable oils such as castor oil, rape oil, olive oil, and sesame oil; surfactants such as polysorbates, sodium lauryl sulfates, and dioctyl-sodium sulfosuccinates; mono acetate of glycerol; diacetate of glycerol; triacetate of glycerol; natural gums; triacetin; acetyltributyl citrate; diethyloxalate; diethylmalate; diethyl fumarate; diethylmalonate; dioctylphthalate; dibutylsuccinate; glyceroltributyrate; hydrogenated castor oil; fatty acids; substituted triglycerides and glycerides. In one embodiment, the coated particle comprises from about 0.1 to about 3 percent, by weight, of plasticizer(s).

In one embodiment, the coating comprises an ionic conductor, such as a salt. Examples of salts include, but are not limited to, metal salts such as sodium, calcium, magnesium, and potassium salts, such as sodium chloride and sodium citrate. In one embodiment, the coated particle comprises from about 0.1 to about 3 percent, by weight, of ion conductors(s).

Q Value

The property of permittivity is the measure of the resistance to forming an electric field. For purposes of comparing materials in air, it is often convenient to describe the permittivity of material in air where the permittivity is more specifically called "relative permittivity" or $\varepsilon_r$. This is a complex number represented by the following equation:

$$\varepsilon_r = e' - je''$$

where e' (the real portion of the complex number) is the dielectric constant (energy storage) and e'' (the imaginary portion of the complex number) is the dielectric loss or dissipation factor (energy dissipated as heat). The ratio of dielectric loss (e'') over the dielectric constant (e') is called the loss tangent (tan δ) or power factor. Since loss tangent values for materials used in foods/pharmaceuticals are very low at 27 MHz, it is convenient to use the reciprocal of loss tangent or "Q value" hence, $$Q\ \text{value} = e'/e''$$

For purposes of this invention, the Q value is calculated for the frequency that the material is to be processed (e.g., 27 MHz). The Q value is affected by physical and chemical properties such as density (porosity/particle size), moisture (conductivity), temperature, and molecular polarizability. The measurements obtained by this method can eliminate the need to measure and evaluate these properties independently.

As the Q value becomes smaller, a material will heat more readily when an external electromagnetic field is applied.

For purposes of describing the components of the invention, a material which has a high Q value (e.g., which responds less to the external field) is referred to as a "passivator." Passivators can serve to insulate or impede energy flow. Conversely, lower Q values (e.g., having higher flux) are termed "activators," as energy is allowed to flow through more easily and do more work. For purposes of describing the present invention, passivators have Q values greater than about 100 (such as greater than 200 or greater than 300), while activators have Q values less than 75 (such as less than 50).

The Q value for various materials is recited below in Table 1. The Q values were measured using a HP 805C Slotted Line as sample holder (carriage removed) connected to Agilent N5230C PNA-L to ports A and B (transmission mode). The sample holder and coaxial wires with N-type connectors are calibrated at room temperature using 8592-60008 E-cal to eliminate error in loss measurement encountered from the coax lines/sample holder itself. This process is referred to as the "Slotted Line Method." Unless otherwise stated, the Slotted line method was used for the calculation of e', e'', and Q value herein with the frequency range set to 26-28 MHz (31 points resolution) and values of e' and e'' were recorded from the 27 MHz data point.

TABLE 1

| Material | Function | e' | e'' | Loss Tangent | Q Value |
|---|---|---|---|---|---|
| Hydroxyethyl cellulose (Natrosol L250), LOD = 4.1% | activator | 2.0937 | 0.1574 | 0.0752 | 13 |
| Hydroxypropyl cellulose (Klucel EF), LOD = 2.3% | activator | 1.7225 | 0.0972 | 0.0564 | 18 |
| Hydroxypropyl cellulose (Klucel ELF), LOD = 1.6% | activator | 1.6404 | 0.0769 | 0.0469 | 21 |
| Hydroxypropyl cellulose (Klucel LF), LOD = 1.8% | activator | 1.5964 | 0.0723 | 0.0453 | 22 |
| Hydroxypropyl cellulose (Klucel JF), LOD = 1.8% | activator | 1.6248 | 0.0739 | 0.0455 | 22 |

TABLE 1-continued

| Material | Function | e' | e" | Loss Tangent | Q Value |
|---|---|---|---|---|---|
| Hydroxypropyl cellulose (SSL-SFP) | activator | 1.4174 | 0.0520 | 0.0367 | 27 |
| Sucrose (Granular Table Sugar) | substrate | 1.9314 | 0.0096 | 0.0050 | 201 |
| Acetaminophen Coated with Ethylcellulose* | substrate | 1.8625 | 0.0050 | 0.0027 | 373 |
| Maltitol (SweetPearl DC300) | substrate | 1.6214 | 0.0035 | 0.0022 | 463 |

*Note -
taste-masked particle has coating but the coating does not have an activator (i.e., the Q value of ethylcellulose was measured to be 98).

In one embodiment, e' of the lossy coated particle (prior to blending) is at least 1.4, such as at least 1.6, such as 1.7 when measured at 27 MHz. In one embodiment, e" of the lossy coated particle (prior to blending) is at least 0.009, such as at least 0.015, such as at least 0.0300 when measured at 27 MHz.

Another method to measure Q value is by using an Agilent 4294A impedance analyzer using specially designed dielectric sample holder. The powder is filled in an empty puck by lightly and evenly pouring in the powder. The excess powder is leveled off to get a flat and even top surface. The first measurement is made by using a thin lid (1 mm) on the powder/puck. In subsequent measurements, the lid is removed and replaced with the next thicker lid. With each lid change, the thickness of the lid increases by 1 mm and the powder is further compressed. When the powder is fully compressed and the lid will not sit flush on the puck, the test is ended. The fully compressed powder along with the puck (without cap) is then weighed. The powder is then removed from the puck and the puck is thoroughly cleaned, to avoid cross contamination, and re-weighed empty to obtain a base weight before and after each different powder test. This allows the tests to be conducted at different powder density, and the tests can be performed at different temperatures, humidity and separate days. This process is referred to as the "Parallel Plate Method." The Q value for various materials is recited below in Table 2

TABLE 2

| Material | Function | e' | e" | Loss Tangent | Q Value |
|---|---|---|---|---|---|
| Polyvinyl Alcohol[1] | activator | 2.4277 | 0.1399 | 0.0576 | 17 |
| Polyvinylalcohol-Polyethylene Glycol Graft Co-Polymer (Kollicoat IR)[2] | activator | 1.9337 | 0.1116 | 0.0577 | 17 |
| Copolymer of ethyl acrylate, methyl methacrylate (Eudragit RL30D)[3] | activator | 1.7496 | 0.0405 | 0.0231 | 43 |
| Povidone (Plasdone ® K12) [4] | activator | 1.7144 | 0.0239 | 0.0139 | 72 |

[1]Available as Emprove ® from EMD Millipore Corporation
[2]Available as Kollicoat IR ® from the BASF Corporation
[3]Available as Eudragit ® RL30D from the Evonik Corporation
[4] Available as Plasdone ® K12 from the Ashland Corporation It has been discovered that coating a substrate comprising one or more passivators with a coating comprising one or more activators resulted in particles were surprising effective in a sintering process of forming very resilient dosage forms with fast disintegration. While not wanting to be bound by this theory, the synergy created by pre-bonding the activator(s) to the passivator (substrate) allows greater efficiency of bonding during sintering beyond simply additive effects.

The substrate has a Q value of greater than 100, such as greater than 150, such as greater than 200, such as greater than 400. The activator has a Q value of less than 75, such as less than 50, such as less than 30. In one embodiment, the lossy coated particle has a Q value of greater than 50, such as greater than 150, such as greater than 200. In one embodiment, the powder blend has a Q value of greater than 50, such as greater than 150, such as greater than 200.

Pharmaceutically Active Agent

The powder blend/tablet of the present invention includes at least one pharmaceutically active agent containing particles. What is meant by a "pharmaceutically active agent" is an agent (e.g., a compound) that is permitted or approved by the U.S. Food and Drug Administration, European Medicines Agency, or any successor entity thereof, for the oral treatment of a condition or disease. Suitable pharmaceutically active agents include, but are not limited to, analgesics, anti-inflammatory agents, antipyretics, antihistamines, antibiotics (e.g., antibacterial, antiviral, and antifungal agents), antidepressants, antidiabetic agents, antispasmodics, appetite suppressants, bronchodilators, cardiovascular treating agents (e.g., statins), central nervous system treating agents, cough suppressants, decongestants, diuretics, expectorants, gastrointestinal treating agents, anesthetics, mucolytics, muscle relaxants, osteoporosis treating agents, stimulants, nicotine, and sedatives.

Examples of suitable gastrointestinal treating agents include, but are not limited to: antacids such as aluminum-containing pharmaceutically active agents (e.g., aluminum carbonate, aluminum hydroxide, dihydroxyaluminum sodium carbonate, and aluminum phosphate), bicarbonate-containing pharmaceutically active agents, bismuth-containing pharmaceutically active agents (e.g., bismuth aluminate, bismuth carbonate, bismuth subcarbonate, bismuth subgallate, and bismuth subnitrate), calcium-containing pharmaceutically active agents (e.g., calcium carbonate), glycine, magnesium-containing pharmaceutically active agents (e.g., magaldrate, magnesium aluminosilicates, magnesium carbonate, magnesium glycinate, magnesium hydroxide, magnesium oxide, and magnesium trisilicate), phosphate-containing pharmaceutically active agents (e.g., aluminum phosphate and calcium phosphate), potassium-containing pharmaceutically active agents (e.g., potassium bicarbonate), sodium-containing pharmaceutically active agents (e.g., sodium bicarbonate), and silicates; laxatives such as stool softeners (e.g., docusate) and stimulant laxatives (e.g., bisacodyl); H2 receptor antagonists, such as famotidine, ranitidine, cimetadine, and nizatidine; proton pump inhibitors such as omeprazole, dextansoprazole, esomeprazole, pantoprazole, rabeprazole, and lansoprazole; gastrointestinal cytoprotectives, such as sucraflate and misoprostol; gastrointestinal prokinetics such as prucalopride; antibiotics for *H. pylori*, such as clarithromycin, amoxicillin, tetracycline, and metronidazole; antidiarrheals, such as bismuth subsalicylate, kaolin, diphenoxylate, and loperamide; glycopyrrolate; analgesics, such as mesalamine; antiemetics such as ondansetron, cyclizine, diphenyhydroamine, dimenhydrinate, meclizine, promethazine, and hydroxyzine; probiotic bacteria including but not limited to lactobacilli; lactase; racecadotril; and antiflatulents such as polydimethylsiloxanes (e.g., dimethicone and simethicone, including those disclosed in U.S. Pat. Nos. 4,906,478, 5,275,822, and 6,103,260); isomers thereof; and pharmaceutically acceptable salts and prodrugs (e.g., esters) thereof.

Examples of suitable analgesics, anti-inflammatories, and antipyretics include, but are not limited to, non-steroidal anti-inflammatory drugs (NSAIDs) such as propionic acid derivatives (e.g., ibuprofen, naproxen, ketoprofen, flurbiprofen, fenbufen, fenoprofen, indoprofen, ketoprofen, fluprofen, pirprofen, carprofen, oxaprozin, pranoprofen, and suprofen) and COX inhibitors such as celecoxib; acetaminophen; acetyl salicylic acid; acetic acid derivatives such as indomethacin, diclofenac, sulindac, and tolmetin; fenamic acid derivatives such as mefanamic acid, meclofenamic acid, and flufenamic acid; biphenylcarbodylic acid derivatives such as diflunisal and flufenisal; and oxicams such as piroxicam, sudoxicam, isoxicam, and meloxicam; isomers thereof; and pharmaceutically acceptable salts and prodrugs thereof.

Examples of antihistamines and decongestants, include, but are not limited to, bromopheniramine, chlorcyclizine, dexbrompheniramine, bromhexane, phenindamine, pheniramine, pyrilamine, thonzylamine, pripolidine, ephedrine, phenylephrine, pseudoephedrine, phenylpropanolamine, chlorpheniramine, dextromethorphan, diphenhydramine, doxylamine, astemizole, terfenadine, fexofenadine, naphazoline, oxymetazoline, montelukast, propylhexadrine, triprolidine, clemastine, acrivastine, promethazine, oxomemazine, mequitazine, buclizine, bromhexine, ketotifen, terfenadine, ebastine, oxatamide, xylomeazoline, loratadine, desloratadine, and cetirizine; isomers thereof; and pharmaceutically acceptable salts and esters thereof.

Examples of cough suppressants and expectorants include, but are not limited to, diphenhydramine, dextromethorphan, noscapine, clophedianol, menthol, benzonatate, ethylmorphone, codeine, acetylcysteine, carbocisteine, ambroxol, belladona alkaloids, sobrenol, guaiacol, and guaifenesin; isomers thereof and pharmaceutically acceptable salts and prodrugs thereof.

Examples of muscle relaxants include, but are not limited to, cyclobenzaprine and chlorzoxazone metaxalone, orphenadrine, and methocarbamol; isomers thereof and pharmaceutically acceptable salts and prodrugs thereof.

Examples of stimulants include, but are not limited to, caffeine.

Examples of sedatives include, but are not limited to sleep aids such as antihistamines (e.g., diphenhydramine), eszopiclone, and zolpidem, and pharmaceutically acceptable salts and prodrugs thereof.

Examples of appetite suppressants include, but are not limited to, phenylpropanolamine, phentermine, and diethylcathinone, and pharmaceutically acceptable salts and prodrugs thereof Examples of anesthetics (e.g., for the treatment of sore throat) include, but are not limited to dyclonine, benzocaine, and pectin and pharmaceutically acceptable salts and prodrugs thereof.

Examples of suitable statins include but are not limited to atorvastin, rosuvastatin, fluvastatin, lovastatin, simvustatin, atorvastatin, pravastatin and pharmaceutically acceptable salts and prodrugs thereof.

In one embodiment, the pharmaceutically active agent included within the tablet is selected from phenylephrine, dextromethorphan, pseudoephedrine, acetaminophen, cetirizine, aspirin, nicotine, ranitidine, ibuprofen, ketoprofen, loperamide, famotidine, calcium carbonate, simethicone, chlorpheniramine, methocarbomal, chlophedianol, ascorbic acid, pectin, dyclonine, benzocaine and menthol, and pharmaceutically acceptable salts and prodrugs thereof.

As discussed above, the pharmaceutically active agents of the present invention may also be present in the form of pharmaceutically acceptable salts, such as acidic/anionic or basic/cationic salts. Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphospate, polygalacturonate, salicylate, stearate, subacetate, succinate, sulfate, tannate, tartrate, teoclate, tosylate and triethiodide. Pharmaceutically acceptable basic/cationic salts include, and are not limited to aluminum, benzathine, calcium, chloroprocaine, choline, diethanolamine, ethylenediamine, lithium, magnesium, meglumine, potassium, procaine, sodium and zinc.

As discussed above, the pharmaceutically active agents of the present invention may also be present in the form of prodrugs of the pharmaceutically active agents. In general, such prodrugs will be functional derivatives of the pharmaceutically active agent, which are readily convertible in vivo into the required pharmaceutically active agent. Conventional procedures for the selection and preparation of suitable prodrug derivatives are described, for example, in "Design of Prodrugs", ed. H. Bundgaard, Elsevier, 1985. In addition to salts, the invention provides the esters, amides, and other protected or derivatized forms of the described compounds.

Where the pharmaceutically active agents according to this invention have at least one chiral center, they may accordingly exist as enantiomers. Where the pharmaceutically active agents possess two or more chiral centers, they may additionally exist as diastereomers. It is to be understood that all such isomers and mixtures thereof are encompassed within the scope of the present invention. Furthermore, some of the crystalline forms for the pharmaceutically active agents may exist as polymorphs and as such are intended to be included in the present invention. In addition, some of the pharmaceutically active agents may form solvates with water (e.g., hydrates) or common organic solvents, and such solvates are also intended to be encompassed within the scope of this invention.

In one embodiment, the pharmaceutically active agent or agents are present in the tablet in a therapeutically effective amount, which is an amount that produces the desired therapeutic response upon oral administration and can be readily determined by one skilled in the art. In determining such amounts, the particular pharmaceutically active agent being administered, the bioavailability characteristics of the pharmaceutically active agent, the dose regime, the age and weight of the patient, and other factors must be considered, as known in the art.

The pharmaceutically active agent may be present in various forms. For example, the pharmaceutically active agent may be dispersed at the molecular level, e.g. melted, within the tablet, or may be in the form of particles, which in turn may be coated or uncoated. If the pharmaceutically active agent is in form of particles, the particles (whether coated or uncoated) typically have an average particle size of from about 1 to about 500 microns. In one embodiment, such particles are crystals having an average particle size of from about 1 to about 300 microns.

The pharmaceutically active agent may be present in pure crystal form or in a granulated form prior to the addition of the taste masking coating. Granulation techniques may be used to improve the flow characteristics or particle size of the pharmaceutically active agents to make it more suitable for subsequent coating. Suitable binders for making the granulation include but are not limited to starch, polyvinylpyrrolidone, polymethacrylates, hydroxypropylmethylcellulose, and hydroxypropylcellulose. The particles including pharmaceutically active agent(s) may be made by cogranulating the pharmaceutically active agent(s) with suitable substrate particles via any of the granulation methods known in the art. Examples of such granulation method include, but are not limited to, high sheer wet granulation and fluid bed granulation such as rotary fluid bed granulation.

If the pharmaceutically active agent has an objectionable taste, the pharmaceutically active agent may be coated with a taste masking coating, as known in the art. Examples of suitable taste masking coatings are described in U.S. Pat. No. 4,851,226, U.S. Pat. No. 5,075,114, and U.S. Pat. No. 5,489,436. Commercially available taste masked pharmaceutically active agents may also be employed. For example, acetaminophen particles, which are encapsulated with ethylcellulose or other polymers by a coacervation process, may be used in the present invention. Coacervation-encapsulated acetaminophen may be purchased commercially from Eurand America, Inc. (Vandalia, Ohio).

In one embodiment, the tablet incorporates modified release coated particles (e.g., particles containing at least one pharmaceutically active agent that convey modified release properties of such agent). As used herein, "modified release" shall apply to the altered release or dissolution of the active agent in a dissolution medium, such as gastrointestinal fluids. Types of modified release include, but are not limited to, sustained release or delayed release. In general, modified release tablets are formulated to make the active agents(s) available over an extended period of time after ingestion, which thereby allows for a reduction in dosing frequency compared to the dosing of the same active agent(s) in a conventional tablet. Modified release tablets also permit the use of active agent combinations wherein the duration of one pharmaceutically active agent may differ from the duration of another pharmaceutically active agent. In one embodiment the tablet contains one pharmaceutically active agent that is released in an immediate release manner and an additional active agent or a second portion of the same active agent as the first that is modified release.

Examples of swellable, erodible hydrophilic materials for use as a release modifying excipient for use in the modified release coating include water swellable cellulose derivatives, polyalkylene glycols, thermoplastic polyalkylene oxides, acrylic polymers, hydrocolloids, clays, and gelling starches. Examples of water swellable cellulose derivatives include sodium carboxymethylcellulose, cross-linked hydroxypropylcellulose, hydroxypropyl cellulose (HPC), hydroxypropylmethylcellulose (HPMC), hydroxyisopropylcellulose, hydroxybutylcellulose, hydroxyphenylcellulose, hydroxyethylcellulose (HEC), hydroxypentylcellulose, hydroxypropylethylcellulose, hydroxypropylbutylcellulose, and hydroxypropylethylcellulose. Examples of polyalkylene glycols include polyethylene glycol. Examples of suitable thermoplastic polyalkylene oxides include poly(ethylene oxide). Examples of acrylic polymers include potassium methacrylatedivinylbenzene copolymer, polymethylmethacrylate, and high-molecular weight cross-linked acrylic acid homopolymers and copolymers.

Suitable pH-dependent polymers for use as release-modifying excipients for use in the modified release coating include: enteric cellulose derivatives such as hydroxypropyl methylcellulose phthalate, hydroxypropyl methylcellulose acetate succinate, and cellulose acetate phthalate; natural resins such as shellac and zein; enteric acetate derivatives such as polyvinylacetate phthalate, cellulose acetate phthalate, and acetaldehyde dimethylcellulose acetate; and enteric acrylate derivatives such as for example polymethacrylate-based polymers such as poly(methacrylic acid, methyl methacrylate) 1:2 (available from Rohm Pharma GmbH under the tradename EUDRAGIT S) and poly(methacrylic acid, methyl methacrylate) 1:1 (available from Rohm Pharma GmbH under the tradename EUDRAGIT L).

In one embodiment the pharmaceutically active agent is coated with a combination of a water insoluble film forming polymer (such as but not limited to cellulose acetate or ethylcellulose) and a water soluble polymer (such as but not limited to povidone, polymethacrylic co-polymers such as those sold under the tradename Eudragit E-100 from Rohm America, and hydroxypropylcellulose). In this embodiment, the ratio of water insoluble film forming polymer to water soluble polymer is from about 50 to about 95 percent of water insoluble polymer and from about 5 to about 50 percent of water soluble polymer, and the weight percent of the coating by weight of the coated taste-masked particle is from about 5 percent to about 40 percent.

In one embodiment, one or more pharmaceutically active agents or a portion of the pharmaceutically active agent may be bound to an ion exchange resin for the purposes of taste-masking the pharmaceutically active agent or delivering the active in a modified release manner.

In one embodiment, the pharmaceutically active agent is capable of dissolution upon contact with a fluid such as water, stomach acid, intestinal fluid or the like. In one embodiment, the dissolution of the tablet containing the pharmaceutically active agent meets USP specifications for immediate release. For example, for acetaminophen tablets, USP 24 specifies that in pH 5.8 phosphate buffer, using USP apparatus 2 (paddles) at 50 rpm, at least 80% of the acetaminophen contained in the tablet is released there from within 30 minutes after dosing, and for ibuprofen tablets, USP 24 specifies that in pH 7.2 phosphate buffer, using USP apparatus 2 (paddles) at 50 rpm, at least 80% of the ibuprofen contained in the tablet is released there from within 60 minutes after dosing. See USP 24, 2000 Version, 19-20 and 856 (1999). In another embodiment, the dissolution characteristics of the pharmaceutically active agent are modified: e.g. controlled, sustained, extended, retarded, prolonged, delayed and the like.

In one embodiment, the pharmaceutically active agent(s) are comprised within polymer-coated particles (e.g., taste-masked and/or sustained release coated particles). In one embodiment, the active ingredient is first coated with a taste-masking coating and subsequently coated with a second layer of a dielectric coating. In one embodiment the pharmaceutically active agent(s) is included within the substrate and/or the coating layer of the lossy coated particle.

In one embodiment, the powder blend/tablet comprises from about 10% to about 40%, by weight of the pharmaceutically active agents(s), such as 15% to about 35%, by weight of the tablet/powder blend, such as 20% to about 30%, by weight of the tablet/powder blend.

As discussed above, in one embodiment, the pharmaceutically active agent is or is comprised within the substrate of the lossy coated particles. In one embodiment, the amount of such coated particles comprising pharmaceutically active agents(s) may be present at level from about 10% to about 95%, by weight of the tablet/powder blend, such as 15% to about 70%, by weight of the tablet/powder blend, such as 20% to about 50%, by weight of the tablet/powder blend.

In one embodiment, the pharmaceutically active agent(s) are comprised within lossy coated particles. In one embodiment, the active ingredient is first coated with a taste-masking coating in absence of an activator and subsequently coated with a second layer containing an activator. In one embodiment the active ingredient is added to the outer coating layer containing an activator.

Forming the Tablet Shape

In one embodiment, to obtain desired attribute of an orally disintegrating tablet, the tablet's construction may be highly porous and/or have a low density (e.g., to allow the tablet to collapse in the oral cavity). In a preferred embodiment, a minimum or no tamping is desired to achieve the orally disintegrating property.

In one embodiment, the tamping step (which occurs prior to the addition of the radiofrequency energy) applies a force to the cavities holding the material to remove air from within the void space between particles and allows material to form into a shape. In one embodiment, the force is less than about 450 pounds per square inch (e.g., less than about 300 pounds per square inch, such as less than 200 pounds per square inch, such as less than 50 pounds per square inch) which comes to rest on a frame (or mechanical "stop") preventing further deformation of material and without the RF energy no tablet is formed. In one embodiment, the energy is applied while the powder blend is under such force without the use of a mechanical stop.

In one embodiment, the tamping step occurs in an indexed manner, where one set of tablets are processed simultaneously, before rotating to another indexing station. In one embodiment, the tamping step occurs at a single indexing station and the application of energy occurs at a separate indexing station. In another embodiment, a third indexing station is present wherein the ejection of the tablet or multiple tablets occurs, wherein the lower forming tool is raised up through and up to the surface of the die. In another embodiment the tamping step is performed through the addition of air pressure or hydraulic cylinder to the top of the upper forming tools. In one embodiment multiple tablets are ejected simultaneously and separated from the surface of the indexing station and removed via a take-off bar.

In another embodiment, the tablet shape may be prepared by methods and apparatus described in United States Patent Application Publication No. 20040156902. Specifically, the tablet shape may be made using a rotary compression module including a fill zone, insertion zone, compression zone, ejection zone, and purge zone in a single apparatus having a double row die construction. The dies of the compression module may then be filled using the assistance of a vacuum, with filters located in or near each die. The purge zone of the compression module includes an optional powder blend recovery system to recover excess powder blend from the filters and return the powder blend to the dies.

In one embodiment, the tablet shape is prepared by the methods and apparatus described in issued U.S. Pat. No. 6,767,200. Specifically, the tablet shape is made using a rotary compression module including a fill zone, compression zone, and ejection zone in a single apparatus having a double row die construction as shown in FIG. 6 therein. The dies of the compression module are preferably filled using the assistance of a vacuum, with filters located in or near each die.

The tablet shape may have one of a variety of different shapes. For example, the tablet shape may be shaped as a polyhedron, such as a cube, pyramid, prism, or the like; or may have the geometry of a space figure with some non-flat faces, such as a cone, truncated cone, triangle, cylinder, sphere, torus, or the like. In certain embodiments, a tablet shape has one or more major faces. For example, the tablet shape surface typically has opposing upper and lower faces formed by contact with the upper and lower forming tool faces (e.g., die punches). In such embodiments, the tablet shape surface typically further includes a "belly-band" located between the upper and lower faces, and formed by contact with the die walls. A tablet shape/tablet may also be a multilayer. Applicants have found that sharp edges in the tooling used to make the tablets can cause arcing, and thus more rounded edges may be needed.

In one embodiment a vibratory step is utilized (e.g., added after filling of the powder blend but prior to the heating or fusing step, in order to remove air from the powder blend). In one embodiment a vibration with the frequency from about 1 Hz to about 50 KHz is added with amplitude from 1 micron to 5 mm peak-to-peak to allow for the flowable powder blend to settle into the cavity of a the die platen ("forming cavity").

Radiofrequency Energy Application to Powder Blend

The process includes the step of applying radiofrequency energy to a powder blend for a sufficient period of time to form such tablet. While not wanting to be bound to any particular theory, it is believed that the pre-bonding of the activator on the surface of a passivator (the substrate) may provide a more direct path for the energy to travel due to higher conductivity at the surface. Such heating may be dielectric heating (e.g., using a lossy polymer containing vinyl, esters, amides, and/or urethane functional groups) or ionic heating. For ionic heating, as the field flows through the blend over the surface of the lossy coated particles, trapped moisture in the powder blend can provide a source of storing energy (e.g., at 27 MHz, pure water has high dielectric constant) for the lossy coating. The higher loss polymer/activator can efficiently use the energy stored from the moisture to soften and flow the polymeric chains to form physical bonds through polymeric chain entanglement. The synergy provided by the configuration of the lossy coated particle can even provide enough bond strength to allow materials which do not provide a conductive path (or contain a lossy material) to be mixed into the lossy coated particle, where the invention serves as a filler.

Radiofrequency heating generally refers to heating with electromagnetic field at frequencies from about 1 MHz to about 100 MHz. In one embodiment of the present invention, the RF-energy is within the range of frequencies from about 1 MHz to about 100 MHz (e.g., from about 5 MHz to 50 MHz, such as from about 10 MHz to about 30 MHz). In one embodiment, the RF-energy is used to heat the first material. RF energy generators are well known in the art. Examples of suitable RF generators include, but are not limited to, free running oscillators such as the COSMOS Model C10X16G4 (Cosmos Electronic Machine Corporation, Farmingdale, N.Y.) or a 50 Ohm RF generator. In one embodiment the RF energy is combined with a second source of heat including but not limited to infrared, induction, or convection heating.

In the embodiment, the electrodes are incorporated into a chamber holding the powder blend (e.g., a cylinder, walled-sheet, or other chamber). In one embodiment, the chamber is constructed of a conductive metal. In one embodiment, the chamber has portions which are constructed of non-conductive, insulative material. In one embodiment, the chamber has an insert which is non-conductive where the body of the chamber is conductive. In one embodiment, the insert comprises a surface area which is less than that of the chamber. The conductive material may be comprised of any material which is conductive, including but not limited to aluminum, copper, iron, zinc, nickel and mixtures and alloys thereof. The non-conductive material may be comprised of a non-conductive solid material including but not limited to ceramics, polystyrene and polytetrafluoroethylene. In one embodiment, the chamber has at least one electrode embedded into the walls of the cylinder or walled sheet. The electrode may be surrounded by non-conductive material wherein the electrode is the only conductive wall portion exposed to the power blend. In one embodiment, the powder blend is tamped prior to the addition of RF-energy.

In one embodiment, one chamber contains the powder blend and it is placed into a separate chamber (e.g., an oven) for the addition of energy. In another embodiment, the chamber containing the powder blend has additional heating elements incorporated into the chamber.

After the application of energy, the powder blend may optionally be cooled (e.g., actively cooled or allowed to cool) prior to forming a predetermined amount of the energy-applied powder blend into the tablet.

Examples of apparatuses useful for such application of energy are set forth in US Patent Application Nos. 20110068511 and 20130295211.

Multi-Layer Tablet

In certain embodiments, the tablet includes at least two layers, e.g., with different types and/or concentrations of the first or second material and/or other ingredients or different concentrations of pharmaceutically active agents. In one embodiment, the tablet includes two layers, one layer having orally disintegrating properties and another layer being chewable or swallowable. In one embodiment one layer is tamped at higher compaction force versus the other layer. In one embodiment, both layers have different amount of pharmaceutically active agents and/or other excipients. In one embodiment, all properties of the two layers are identical but the colors of the two layers are different. In one embodiment, not all of the layers comprise the coated particle (e.g., only one of the two layers). In one embodiment, two layers of the dosage form comprise the coated particle, but the compositions of the coated particle (e.g., the materials and/or the relative amounts of the materials comprising the coated particles) are different.

Effervescent Couple

In one embodiment, the powder blend/tablet further contains one or more effervescent couples. In one embodiment, effervescent couple contains one member from the group consisting of sodium bicarbonate, potassium bicarbonate, calcium carbonate, magnesium carbonate, and sodium carbonate, and one member selected from the group consisting of citric acid, malic acid, fumaric acid, tartaric acid, phosphoric acid, and alginic acid.

In one embodiment, the combined amount of the effervescent couple(s) in the powder blend/tablet is from about 2 to about 20 percent by weight, such as from about 2 to about 10 percent by weight of the total weight of the powder blend/tablet.

Orally Disintegrating Tablet

In one embodiment, the tablet is designed to disintegrate in the mouth when placed on the tongue in less than about 60 seconds, e.g. less than about 45 seconds, e.g. less than about 30 seconds, e.g. less than about 15 seconds.

In one embodiment, the tablet meets the criteria for Orally Disintegrating Tablets (ODTs) as defined by the draft Food and Drug Administration guidance, as published in April, 2007. In one embodiment, the tablet meets a two-fold definition for orally disintegrating tablets including the following criteria: 1) that the solid tablet is one which contains medicinal substances and which disintegrates rapidly, usually within a matter of seconds, when placed upon the tongue and 2) be considered a solid oral preparation that disintegrates rapidly in the oral cavity, with an in vitro disintegration time of approximately 30 seconds or less, when based on the United States Pharmacopeia (USP 24 NF 29) disintegration test method for the specific medicinal substance or substances.

Tablets Coatings

In one embodiment, the tablet includes an additional outer coating (e.g., a translucent coating such as a clear coating) to impart additional properties to the dosage form. Suitable materials for such coatings include, but are not limited to, hypromellose, hydroxypropylcellulose, starch, polyvinyl alcohol, polyethylene glycol, polyvinylalcohol and polyethylene glycol mixtures and copolymers, and mixtures thereof. Tablets of the present invention may include a coating from about 0.05 to about 10 percent, or about 0.1 to about 5 percent by weight of the total tablet.

Hardness, Friability, and Density of Tablet

In one embodiment, the tablet is prepared such that the tablet is relatively soft (e.g., capable of disintegrating in the mouth or being chewed). The hardness test (crushing hardness) is based on hardness of the dosage form measured perpendicular to the cross-section at the belly band using a modified Model 6d, Pharmatron hardness tester fitted with a 50 g force load cell (lower forces required for testing the invention). Unless otherwise indicated, testing is conducted on two stacked tablets, and the hardness is reported as 50% of the hardness measured. In one embodiment, the hardness of the tablet is less than 1 kiloponds, such as less than 0.5 kiloponds.

In one embodiment, the density of the tablet is at least about 0.6 g/cc. In one embodiment, the density of the tablet is less than about 1.5 g/cc. In one embodiment, the bulk density of the lossy coated particles is from about 0.5 g/cc to about 1 g/cc.

In one embodiment, the tablets have a friability of less than 10 percent, such as less than 5 percent, such as less than 3 percent. As used herein, "friability" is measured using the USP 24 NF 29 Tablet Friability (Section 1216) with the modification of using 3 tablets for 15 rotations or 3 tablets for 100 revolutions (unless otherwise noted) instead of 10 tablets for 100 rotations.

Use of Tablet

The tablets may be used as swallowable, chewable, or orally disintegrating tablets to administer the pharmaceutically active agent.

In one embodiment, the present invention features a method of treating an ailment, the method including orally administering the above-described tablet wherein the tablet includes an amount of the pharmaceutically active agent effective to treat the ailment. Examples of such ailments include, but are not limited to, pain (such as headaches, migraines, sore throat, cramps, back aches and muscle aches), fever, inflammation, upper respiratory disorders (such as cough and congestion), infections (such as bacterial and viral infections), depression, diabetes, obesity, cardiovascular disorders (such as high cholesterol, triglycerides, and blood pressure), gastrointestinal disorders (such as nausea, diarrhea, irritable bowel syndrome and gas), sleep disorders, osteoporosis, and nicotine dependence.

In one embodiment, the method is for the treatment of an upper respiratory disorder, wherein the pharmaceutically active agent is selected from the group of phenylephrine, cetirizine, loratadine, fexofenadine, diphenhydramine, dextromethorphan, chlorpheniramine, chlophedianol, and pseudoephedrine.

In this embodiment, the "unit dose" is typically accompanied by dosing directions, which instruct the patient to take an amount of the pharmaceutically active agent that may be a multiple of the unit dose depending on, e.g., the age or weight of the patient. Typically the unit dose volume will contain an amount of pharmaceutically active agent that is therapeutically effective for the smallest patient. For example, suitable unit dose volumes may include one tablet.

EXAMPLES

Specific embodiments of the present invention are illustrated by way of the following examples. This invention was not confined to the specific limitations set forth in these examples.

Example 1: Preparation of Hydroxypropylcellulose (HPC) Coated Mannitol Particles and Resulting Tablet Part A: Production of Lossy Coated Particles:

A batch of 14 kg of HPC coated mannitol particles was prepared according to the procedure below. These lossy coated particles were then used to produce the orally disintegrating tablets in Part B.

Lossy Coating Solution:
1. Purified Water USP was added to a suitably sized stainless steel container.
2. Hydroxypropylcellulose ("HPC", commercially available from Ashland Specialty Ingredients as Klucel® EF), as an activator, was added with gentle agitation at concentration of 4% solid in solution.

Coating of Substrate Particles (as a passivator) with Lossy Coating Solution:
1. 14000 g of mannitol, as a substrate, was added to a fluid bed, Aeromatic S2 (GEA Group) top spray granulator.
2. The Lossy Coating Solution was sprayed onto the Mannitol at a spray rate of 50 g/minute to a concentration of 0.6% weight/weight to a percent moisture of 10.4% utilizing loss on drying.
3. The coated particles were further dried to a percent moisture utilizing loss on drying of approximately 0.38%.

Part B: Tablet Formulation using HPC Coated Particles:

The lossy coated particles of Part A were filled into 12.5 mm round dies and sintered at a radio frequency of approximately 27 MHz for 0.8 seconds ("Sintering Time" of 0.8 seconds) to form an orally disintegrating tablet using a machine as disclosed in US Patent No. 20130295211. The electrode distance and variable capacitor was adjusted to remove air from void spaces while optimizing tuning to the tank circuit to provide adequate power transfer through material to form the tablet without causing arcing or flashing. Information regarding the resulting tablets are set forth in Tables 4-7.

Comparative Example 2: Preparation of Tablets with Activator and Passivator Prepared as a Dry Blend of Separate Particles Tablets were produced to demonstrate the difference between tablets produced with HPC coated mannitol particles (as in Example 1) and those made using a dry blend of HPC (activator) and maltitol particles (passivator). The blend of HPC and maltitol particles were blended in a rigid sealed polystyrene container placed on a Turbula® mixer (Impandex, Inc. Maywood, N.J.) for five minutes. The results are reported in Table 2B.

TABLE 2B

| Example | % w/w HPC particles | % w/w maltitol | Oral DT* | USP DT[1] | Q value | Result (Friability % at 15 drops) |
|---|---|---|---|---|---|---|
| Example 2A | 1.0 | 99.0 | n/a | n/a | 569 | Too friable to handle |
| Example 2B | 2.0 | 98.0 | n/a | n/a | 402 | Too friable to handle |
| Example 2C | 5.0 | 95.0 | n/a | n/a | 197 | Too friable to handle |
| Example 2D | 10.0 | 90.0 | n/a | n/a | 79 | Too friable to handle |
| Example 2E | 15.0 | 85.0 | n/a | n/a | 66 | 11 |
| Example 2F | 20.0 | 80.0 | n/a | n/a | 57 | 4.2 |
| Example 2G | 22.0 | 78.0 | 38 | 42 | 47 | 3.1 |

*DT—Disintegration Time
[1]Disintegration time as determined by tablet disintegration for the United States Pharmacopeia USP 24
n/a—not applicable For dry blends below 10% w/w HPC, the resulting tablets were too friable to handle. For blends prepared at 15 to 20% w/w HPC, the resulting tablets could be sintered using radiofrequency energy and formed, but the resulting tablets were still very friable. For tablets at 22% HPC, the resulting tablets had an acceptable friability of 3.1%, but disintegration times were greater than 30 seconds, which is undesirable for an orally disintegrating tablet and does not meet USP requirements. Modifying manufacturing settings of time, tamp and tuning did not overcome the resulting long disintegration times, thus demonstrating the unexpected benefit of coating the passivator particles with the activator rather than merely blending them as separate particles.

Example 3: Preparation of Hydroxyethylcellulose (HEC) Coated Mannitol Particles Part A: Production of Lossy Coated Particles:

A batch of 14 kg of HEC coated mannitol particles was prepared according to the procedure below. These lossy coated particles were then used to produce the orally disintegrating tablets in Example 3, Part B.

Lossy Coating Solution:
1. Purified Water USP added to a suitably sized stainless steel container.
2. Hydroxyethylcellulose (commercially available as Natrosol 250 from Ashland Specialty Ingredients), as an activator, was added with gentle agitation at concentration of 4% solids in solution.

Coating of Substrate Particles with Lossy Coating Solution:
3. 14000 g of Mannitol, as a substrate, was added to a fluid bed, top spray granulator.

4. The Lossy Coating Solution was sprayed onto the Mannitol at a spray rate of 50 g/minute to a concentration of 0.5% weight/weight to percent moisture of 2.7% utilizing loss on drying.
5. The granules were further dried to a percent moisture utilizing loss on drying of approximately 0.18%.

Part B: Tablet Formulation Using Hydroxyethylcellulose Coated Particles with Acetaminophen:

Tablets were produced at a weight of 566 mg, according to the formula in Table 3. The blend was filled into 12.5 mm round dies and sintered at a radio frequency of 27 MHz for approximately 0.8 seconds to form an orally disintegrating tablet using the process of Example 1. The disintegration time as measured by USP 24 was less than 30 seconds and the friability of the tablets was less than 3 percent (15 drops of 3 tablets).

TABLE 3

| Granulation Blend | % w/w | Mg/Tablet |
|---|---|---|
| Coated Mannitol Particles - Example 3, Part A | 84.0 | 472.7 |
| Coated Acetaminophen[1] (90% potency) | 16.0 | 93.3 |
| TOTAL | 100.0 | 566.0 |

[1]Available from the Aptalis Corporation as Acetaminophen Microcaps ®

Example 4: Variations in Amounts of Lossy Coating and Types of Substrates

Multiple batches of lossy coated particles were prepared, and tablets were prepared both with and without the further addition of pharmaceutically active agents. Information regarding these batches is described below in Tables 4-7. Disintegration time is reported as an oral (in vitro) taste-test, as well as using the United States Pharmacopeia tablet test for disintegration (USP 24). With respect to Tables 4-7: (i) dextrose was added as dextrose monohydrate; (ii) PE means phenylephrine HCl; (iii) DPH means diphenhydramine; APAP means acetaminophen; and N/A means not available. The method of calculating the geometric mean diameter was via sieve analysis was an ATM Sonic sifter, which is commercially available from by the Sepor Corporation. For the ATM Sonic sifter analysis, about 10 g of material is used. Alternatively, for larger sample sizes, the FMC Sieve Shaker is used, which is commercially available from the FMC Corporation. For the FMC Sieve Shaker analysis, about 100 g of material is used.

Example 4A

Lossy coated particles were prepared utilizing the procedure in Example 1 utilizing 0.5% weight/weight of hydroxypropylcellulose (Klucel® EF). Phenylephrine was added to the coating solution for the coated mannitol for a level of 12.1 mg dosage in the final form. Tablets were prepared at a tablet weight of 169 mg and sintered for 1.5 seconds.

Example 4B

Lossy coated particles were prepared utilizing the procedure in Example 1 wherein erythritol was substituted in lieu of mannitol as the substrate. The level of hydroxypropylcellulose (activator) was increased to 0.7% weight/weight. Tablets were prepared at a tablet weight of 486 mg and sintered for 0.8 seconds.

Example 4C

The coated erythritol particle from Example 4B was blended with coated Diphenhydramine HCl at a dose of 40.5 mg per tablet. Tablets were prepared at 482 mg and sintered for 1.5 seconds.

Example 4D

The coated mannitol particle from Example 1 was prepared with an additional 0.17% weight/weight of sodium chloride was added to the coating solution, at a hydroxypropylcellulose concentration of 0.5% weight/weight. Tablets were prepared at a tablet weight of 383 mg and sintered for 1.0 seconds.

Example 4E

Lossy coated particles were prepared using the procedure from Example 1 with dextrose monohydrate used in lieu of mannitol as the substrate. Hydroxypropylcellulose was added at a level of 0.5% weight/weight. Tablets were prepared at a weight of 532 mg and sintered for 1.0 seconds.

Example 4F

Lossy coated mannitol particles were prepared utilizing the procedure in Example 1 by increasing the level of hydroxypropylcellulose to 0.8% by weight of the coated mannitol. Tablets were prepared without active ingredient in the blend, at a tablet weight of 397 mg and sintered at 0.5 seconds.

Example 4G

Lossy coated mannitol particles were prepared utilizing the procedure in Example 1 by increasing the level of hydroxypropylcellulose to 0.9% by weight of the coated mannitol. Tablets were prepared without active ingredient in the blend, at a tablet weight of 397 mg and sintered at 0.5 seconds.

Example 4H

Lossy coated mannitol particles were prepared utilizing the procedure in Example 1 by increasing the level of hydroxypropylcellulose to 0.9% by weight of the coated mannitol. The coated mannitol was blended with 10% weight/weight of erythritol powder. Tablets were prepared without active ingredient in the blend, at a tablet weight of 407 mg and sintered at 0.5 seconds.

Example 4I

Lossy coated mannitol particles were prepared utilizing the procedure in Example 1 by increasing the level of hydroxypropylcellulose to 0.9% by weight of the coated mannitol. The coated mannitol was blended with encapsulated acetaminophen at a dose of 37 mg. Tablets were prepared without active ingredient in the blend, at a tablet weight of 416 mg and sintered at 1.0 seconds.

Example 4J

Lossy coated particles were prepared utilizing the procedure in Example 4I by using a grade of hydroxypropylcellulose with a lower molecular weight (approximately 40,000

Daltons under the tradename of Nisso® SSL from Nippon Soda Co.) at a weight of 0.9% by weight of the coated mannitol. Tablets were prepared without an active ingredient in the blend, at a tablet weight of 389 mg and sintered at 0.5 seconds.

Example 4K

Lossy coated particles were prepared using the procedure from Example 1 with maltitol in lieu of mannitol as the substrate. Maltitol is used as an example of a hygroscopic sugar. Hydroxypropylcellulose was added at a level of 0.9% by weight of the coated maltitol. Tablets were prepared at a weight of 661 mg and sintered for 1.0 seconds.

Example 4L

Lossy coated particles were prepared using the procedure from Example 1 with maltitol in lieu of mannitol as the substrate and at a level of Hydroxypropylcellulose of 0.9% of the coated maltitol. Glyceryl monostearate (GMS) was added as an adjunct to the coated maltitol in the coating solution at a level of 0.18% by weight of the coated maltitol. Tablets were prepared without active ingredient in the blend, at a tablet weight of 578 mg and sintered at 0.5 seconds.

Example 4M

Lossy coated particles were prepared using the procedure from Example 1 with maltitol in lieu of mannitol as the substrate. Hydroxypropylcellulose was added at a level of 0.9% by weight of the coated maltitol. Tablets were prepared at a weight of 631 mg and sintered for 1.5 seconds.

Example 4N

Lossy coated particles were prepared using the procedure from Example 1 with maltitol in lieu of mannitol as the substrate. Hydroxypropylcellulose was added at a level of 0.9% by weight of the coated maltitol. Encapsulated acetaminophen was added at a dose of 155 mg. Tablets were prepared at 609 mg and sintered for 1.5 seconds.

Example 4O

Lossy coated particles were prepared using the procedure from Example 1 with maltitol in lieu of mannitol as the substrate. Hydroxypropylcellulose was added at a level of 0.9% by weight of the coated maltitol. Encapsulated acetaminophen was added at a dose of 160 mg. Tablets were prepared at a weight of 625 mg and sintered for 1.5 seconds.

Example 4P

Lossy coated particles were prepared using the procedure from Example 1 with maltitol in lieu of mannitol as the substrate. Hydroxypropylcellulose was added at a level of 1.2% by weight of the coated mannitol. Tablets were prepared at a weight of 546 mg and sintered for 1.5 seconds.

Example 4Q

Lossy coated particles were prepared utilizing the procedure in Example 1 using a level of Hydroxypropylcellulose of 1.2% by weight of the coated mannitol. Encapsulated acetaminophen was added at a dose of 160 mg. Tablets were prepared at tablet weight of 694 mg and sintered at 1.5 seconds. These tablets had an oral disintegration time of 32 seconds.

Example 4R

Lossy coated particles were prepared utilizing the procedure in Example 1 using a level of Hydroxypropylcellulose of 1.0% by weight of the coated mannitol. Encapsulated acetaminophen was added at a dose of 325 mg. Tablets were prepared at tablet weight of 807 mg and sintered at 0.5 seconds.

Example 4S

Lossy coated particles were prepared utilizing the procedure in Example 1, by lowering the level of Hydroxypropylcellulose to 0.4% by weight of the coated mannitol. Encapsulated acetaminophen was added at a dose of 137 mg. Tablets were prepared at tablet weight of 509 mg and sintered at 0.5 seconds.

Example 4T

Lossy coated particles were prepared utilizing the procedure in Example 1 by lowering the level of Hydroxypropylcellulose to 0.4% by weight of the coated mannitol. Encapsulated acetaminophen was added at a dose of 128 mg. Tablets were prepared at tablet weight of 475 mg and sintered at 0.5 seconds. These tablets has a friability of greater than 2.0 percent (3.9 percent) at 15 drops.

TABLE 4

| Material/Output | Example 1 | Example 4A | Example 4B | Example 4C | Example 4D | Example 4E |
|---|---|---|---|---|---|---|
| Substrate | Mannitol | Mannitol | Erythritol | Erythritol | Mannitol | Dextrose |
| Substrate Geometric Mean Diameter (μm) | 112 | 112 | 289 | 289 | 112 | 130 |
| Activator | HPC (Klucel EF) | HPC (Klucel EF) | HPC (Klucel EF) | HPC (Klucel EF) | HPC (Klucel EF) + NaCl | HPC (Klucel EF) |
| Activator Concentration (% w/w) | 0.6 | 0.5 | 0.7 | 0.7 | 0.5 | 0.5 |
| Pharmaceutically Active Agent | None | PE | None | DPH | None | None |
| Active Dose per tablet | N/A | 12.1 | N/A | 40.5 | n/a | n/a |
| % Lossy Coated Particles in Powder Blend | N/A | 100.0 | 100.0 | 90.0 | 100.0 | 100.0 |
| % Moisture at End of Spraying | 10.4 | 2.7 | 2.2 | 2.2 | 13.4 | 13.0 |

TABLE 4-continued

| Material/Output | Example 1 | Example 4A | Example 4B | Example 4C | Example 4D | Example 4E |
|---|---|---|---|---|---|---|
| % Moisture of Lossy Coated Particles Before Sintering | 0.38 | 0.8 | 0.93 | n/a | 0.14 | 9.05 |
| Lossy Coated Particle Geometric Mean Diameter (μm) | 154 | n/a | n/a | n/a | n/a | n/a |
| Tablet Diameter (mm) | 12.5 | 9.5 | 12.5 | 12.5 | 12.5 | 12.5 |
| Tablet Weight (mg) | 393 | 169 | 486 | 482 | 383 | 532 |
| Tablet Thickness (mm) | 4.34 | 3.21 | 4.80 | 4.82 | 4.24 | 4.96 |
| Tablet Volume (cc) | 0.53 | 0.23 | 0.59 | 0.59 | 0.52 | 0.61 |
| Tablet Density (g/cc) | 0.74 | 0.74 | 0.83 | 0.81 | 0.74 | 0.87 |
| Sintering Time (sec) | 0.5 | 1.5 | 0.8 | 1.5 | 1.0 | 1.0 |
| Oral Disintegration Time (sec) | 22 | 4 | 6 | 6 | n/a | 8 |
| USP Disintegration Time (sec) | 9 | n/a | n/a | n/a | 7 | 9 |
| Crushing Hardness (kp) | 0.46 | 0.25 | n/a | n/a | n/a | n/a |
| Friability % (10 drops) | n/a | 1.7 | 0.2 | 1.4 | n/a | n/a |
| Friability % (15 drops) | 0.1 | 2.4 | 0.4 | 1.4 | 0.4 | 1.4 |
| Friability % (100 drops) | 0.2 | n/a | 3.1 | 13.0 | 0.6 | n/a |

TABLE 5

| Material/Output | Example 4F | Example 4G | Example 4H | Example 4I | Example 4J | Example 4K |
|---|---|---|---|---|---|---|
| Substrate | Mannitol | Mannitol | Mannitol | Mannitol | Mannitol | Maltitol |
| Substrate Geometric Mean Diameter (μm) | 112 | 112 | 112 | 112 | 112 | 218 |
| Activator | HPC (Klucel EF) | HPC (Klucel EF) | HPC (Klucel EF) | HPC (Klucel EF) | HPC (Nisso SSL) | HPC (Klucel EF) |
| Activator Concentration (% w/w) | 0.8 | 0.9 | 0.9 | 0.9 | 0.9 | 0.9 |
| Pharmaceutically Active Agent | None | None | None | APAP | None | None |
| Active Dose per tablet | N/A | N/A | N/A | 37.0 | n/a | n/a |
| % Lossy Coated Particles in Powder Blend | 100.0 | 100.0 | 90.0 | 90.0 | 100.0 | 100.0 |
| % Moisture at End of Spraying | 9.0 | 10.5 | 10.5 | 10.5 | 10.9 | 1.7 |
| % Moisture of Lossy Coated Particles Before Sintering | 0.5 | 0.5 | 0.37 | 0.31 | 0.14 | 0.43 |
| Lossy Coated Particle Geometric Mean Diameter (μm) | 135 | 151 | n/a | n/a | n/a | n/a |
| Tablet Diameter (mm) | 12.5 | 12.5 | 12.5 | 12.5 | 12.5 | 12.5 |
| Tablet Weight (mg) | 397 | 397 | 407 | 416 | 389 | 661 |
| Tablet Thickness (mm) | 4.50 | 4.24 | 4.27 | 4.24 | 4.31 | 5.37 |
| Tablet Volume (cc) | 0.55 | 0.52 | 0.52 | 0.52 | 0.53 | 0.66 |
| Tablet Density (g/cc) | 0.72 | 0.76 | 0.78 | 0.80 | 0.74 | 1.00 |
| Sintering Time (sec) | 0.5 | 0.5 | 0.5 | 1.0 | 0.5 | 1.0 |
| Oral Disintegration Time (sec) | 16 | 15 | 11 | 14 | 8 | 10 |
| USP Disintegration Time (sec) | n/a | n/a | n/a | n/a | n/a | n/a |
| Crushing Hardness (kp) | 0.44 | 0.50 | 0.37 | 0.38 | 0.32 | 0.43 |
| Friability % (10 drops) | n/a | n/a | n/a | n/a | n/a | n/a |
| Friability % (15 drops) | 0.2 | 0.1 | 0.0 | 0.2 | 0.2 | 0.3 |
| Friability % (100 drops) | 0.58 | 0.8 | 4.0 | 2.2 | n/a | 0.8 |

TABLE 6

| Material/Output | Example 4L | Example 4M | Example 4N | Example 4O | Example 4P | Example 4Q |
|---|---|---|---|---|---|---|
| Substrate | Maltitol | Maltitol | Maltitol | Maltitol | Maltitol | Mannitol |
| Substrate Geometric Mean Diameter (μm) | 218 | 218 | 218 | 218 | 218 | 132 |
| Activator | HPC (Klucel EF) + GMS | HPC (Klucel EF) | HPC (Klucel EF) | HPC (Klucel EF) | HPC (Klucel EF) | HPC (Klucel EF) |

TABLE 6-continued

| Material/Output | Example 4L | Example 4M | Example 4N | Example 4O | Example 4P | Example 4Q |
|---|---|---|---|---|---|---|
| Activator Concentration (% w/w) | 0.9 | 0.9 | 0.9 | 0.9 | 1.2 | 1.2 |
| Pharmaceutically Active Agent | None | None | APAP | APAP | None | APAP |
| Active Dose per tablet | N/A | N/A | 155 | 160 | n/a | 160 |
| % Lossy Coated Particles in Powder Blend | 100.0 | 100.0 | 72.0 | 72.0 | 100.0 | 56.0 |
| % Moisture at End of Spraying | 3.7 | 3.8 | 3.8 | 3.8 | 2.1 | 16.5 |
| % Moisture of Lossy Coated Particles Before Sintering | n/a | 1.0 | 0.37 | 0.44 | 0.65 | 0.68 |
| Lossy Coated Particle Geometric Mean Diameter (μm) | n/a | 281 | n/a | n/a | n/a | 156 |
| Tablet Diameter (mm) | 12.5 | 12.5 | 12.5 | 12.5 | 12.5 | 12.5 |
| Tablet Weight (mg) | 578 | 631 | 609 | 625 | 546 | 694 |
| Tablet Thickness (mm) | 4.39 | 4.74 | 5.08 | 4.86 | 4.00 | 5.93 |
| Tablet Volume (cc) | 0.54 | 0.58 | 0.62 | 0.60 | 0.49 | 0.73 |
| Tablet Density (g/cc) | 1.07 | 1.08 | 0.98 | 1.05 | 1.11 | 0.95 |
| Sintering Time (sec) | 0.5 | 1.5 | 1.0 | 1.5 | 1.5 | 1.5 |
| Oral Disintegration Time (sec) | 9 | 7 | 10 | 6 | 6 | 32 |
| USP Disintegration Time (sec) | n/a | n/a | n/a | n/a | n/a | n/a |
| Crushing Hardness (kp) | 0.63 | 0.35 | n/a | n/a | 0.27 | 0.54 |
| Friability % (10 drops) | n/a | n/a | n/a | n/a | n/a | n/a |
| Friability % (15 drops) | 0.4 | 0.2 | 2.3 | 0.4 | 0.2 | 1.4 |
| Friability % (100 drops) | n/a | n/a | n/a | n/a | n/a | n/a |

TABLE 7

| Material/Output | Example 4R | Example 4S | Example 4T |
|---|---|---|---|
| Substrate | Mannitol | Mannitol | Mannitol |
| Substrate Geometric Mean Diameter (μm) | 132 | 132 | 132 |
| Activator | HPC (Klucel EF) | HPC (Klucel EF) | HPC (Klucel EF) |
| Activator Concentration (% w/w) | 1.0 | 0.4 | 0.4 |
| Pharmaceutically Active Agent | APAP | APAP | APAP |
| Active Dose per tablet | 325 | 137 | 128 |
| % Lossy Coated Particles in Powder Blend | 41 | 70 | 70 |
| % Moisture at End of Spraying | 10.3 | 4.8 | 4.8 |
| % Moisture of Lossy Coated Particles Before Sintering | 0.22 | 0.71 | 0.71 |
| Lossy Coated Particle Geometric Mean Diameter (μm) | 152 | n/a | 152 |
| Tablet Diameter (mm) | 12.5 | 12.5 | 12.5 |
| Tablet Weight (mg) | 807 | 509 | 475 |
| Tablet Thickness (mm) | 7.56 | 4.40 | 4.83 |
| Tablet Volume (cc) | 0.93 | 0.54 | 0.59 |
| Tablet Density (g/cc) | 0.87 | 0.94 | 0.80 |
| Sintering Time (sec) | 0.5 | 0.5 | 0.50 |
| Oral Disintegration Time (sec) | 27 | 8 | 9 |
| USP Disintegration Time (sec) | n/a | 6 | 5 |
| Crushing Hardness (kp) | 0.36 | 0.30 | 0.28 |
| Friability % (10 drops) | n/a | n/a | n/a |
| Friability % (15 drops) | 2.5 | 1.9 | 3.9 |
| Friability % (100 drops) | n/a | n/a | n/a |

Example 5: Production of Lossy Coated Particles Using 80,000 Daltons MW 1% Hydroxypropylcellulose A batch of 6.1 kg of lossy coated maltitol particles was prepared according to the procedure below. The lossy coated particles were dielectrically characterized using the Slotted line method and reported in Table 8A. These lossy coated particles were then used to produce the orally disintegrating tablets in Examples 5A-G (Table 8A and 8B).

Lossy Coating Solution:
1. Purified Water USP was added to a suitably sized stainless steel container.
2. 60 g of hydroxypropyl cellulose (commercially available as Klucel® EF from Ashland Specialty Ingredients), as an activator, was added with gentle agitation to make a concentration of 4% solids in solution.

Coating of Substrate Particles with Hydroxypropylcellulose Coating Solution:
3. 6000 g of maltitol was added to a fluid bed, top spray granulator.
4. The Lossy Coating solution was sprayed onto the Mannitol at an approximate average spray rate of 115 g/minute to make a 1.0% (w/w) lossy coated particles to a target end of spray percent moisture as noted in Table 8A as measured by loss on drying.
5. The lossy coated particles were then further dried to percent moisture as recorded in Table 8A.

Examples 5A-G: Production of Lossy Coated Particles Using 80,000 Daltons 1% Hydroxypropylcellulose as Activator Lossy coated particles were prepared utilizing the procedure in Example 5, utilizing 1.0% of weight gain of Hydroxypropylcellulose. The lossy coated particles were blended with coated APAP (90% potency) to a concentration of 20%, 30%, 40%, or 50% to make 80, 160 or 325 mg acetaminophen dose tablets (see Tables 8A and 8B).

TABLE 8A

| Material/Output | Example 5 | Example 5A | Example 5B | Example 5C |
|---|---|---|---|---|
| Comment | RF Excipient alone | Blended with APAP Particles | Blended with APAP Particles | Blended with APAP Particles |
| Substrate | Maltitol | Maltitol | Maltitol | Maltitol |
| Activator | HPC | HPC | HPC | HPC |
| Activator Concentration (% w/w) | 1.0 | 1.0 | 1.0 | 1.0 |
| Average Molecular Weight of Polymer (×1000 Daltons) | 80 | 80 | 80 | 80 |
| Pharmaceutically Active Agent | None | APAP | APAP | APAP |
| Active Dose per tablet | N/A | 80 | 80 | 160 |
| % Lossy Coated Particles in Powder Blend | N/A | 20 | 30 | 30 |
| % Moisture at End of Spraying | 1.4 | N/A | N/A | N/A |
| % Moisture of Lossy Coated Particles Before Sintering | 1.4 | 0.79 | 0.79 | 0.79 |
| e' | 1.7256 | 1.6830 | 1.6957 | 1.6957 |
| e" | 0.0132 | 0.0115 | 0.0100 | 0.0100 |
| Q value | 131 | 146 | 170 | 170 |
| Lossy Coated Particle Geometric Mean Diameter (μm) | 302 | N/A | N/A | N/A |
| Tablet Diameter (mm) | 12.5 | 12.5 | 12.5 | 12.5 |
| Tablet Weight (mg) | N/A | 444 | 296 | 593 |
| Tablet Thickness (mm) | N/A | 3.88 | 2.66 | 4.94 |
| Tablet Density (g/cc) | N/A | 0.9 | 0.9 | 0.9 |
| Sintering Time (sec) | N/A | 0.5 | 0.5 | 0.5 |
| Oral Disintegration Time (sec) | N/A | 9 | 4 | 15 |
| Friability % (15 drops) | N/A | 0.4 | 0.2 | 0.6 |
| Friability % (100 drops) | N/A | broke | 1.3 | 2.0 |

TABLE 8B

| Material/Output | Example 5D | Example 5E | Example 5F | Example 5G |
|---|---|---|---|---|
| Comment | Blended with APAP Particles | Blended with APAP Particles | Blended with APAP Particles | Blended with APAP Particles |
| Substrate | Maltitol | Maltitol | Maltitol | Maltitol |
| Activator | HPC | HPC | HPC | HPC |
| Activator Concentration (% w/w) | 1.0 | 1.0 | 1.0 | 1.0 |
| Average Molecular Weight of Polymer (×1000 Daltons) | 80 | 80 | 80 | 80 |
| Pharmaceutically Active Agent | APAP | APAP | APAP | APAP |
| Active Dose per tablet | 160 | 325 | 160 | 325 |
| % Lossy Coated Particles in Powder Blend | 40 | 40 | 50 | 50 |
| % Moisture at End of Spraying | N/A | N/A | N/A | N/A |
| % Moisture of Lossy Coated Particles Before Sintering | 0.58 | 0.60 | 0.41 | 0.41 |
| e' | 1.6970 | 1.6970 | 1.7037 | 1.7037 |
| e" | 0.0094 | 0.0094 | 0.0081 | 0.0081 |
| Q value | 181 | 181 | 210 | 210 |
| Lossy Coated Particle Geometric Mean Diameter (μm) | N/A | N/A | N/A | N/A |
| Tablet Diameter (mm) | 12.5 | 12.5 | 12.5 | 12.5 |
| Tablet Weight (mg) | 444 | 1000 | 356 | 722 |
| Tablet Thickness (mm) | 3.71 | 7.80 | 3.45 | 6.37 |
| Tablet Density (g/cc) | 0.9 | 1.1 | 0.8 | 0.9 |
| Sintering Time (sec) | 1.0 | 1.5 | 1.5 | 1.5 |
| Oral Disintegration Time (sec) | 8 | 20 | N/A | N/A |
| Friability % (15 drops) | 0.4 | 1.2 | Broke | broke |
| Friability % (100 drops) | 1.3 | broke | N/A | N/A |

Examples 6: Production of Lossy Coated Particles Using 40,000 Daltons MW, 1% Hydroxypropyl Cellulose A batch of 6.1 kg of lossy coated maltitol particles was prepared according to the procedure below. The lossy coated particles were dielectrically characterized using the Slotted line method and reported in Table 8A. These lossy coated particles were then used to produce the orally disintegrating tablets in Examples 6A-G (Table 9A and 9B).

Lossy Coating Solution:
1. Purified Water USP was added to a suitably sized stainless steel container.
2. 60 g of hydroxypropyl cellulose (commercially available as Klucel® ELF from Ashland Specialty Ingredients), as an activator, was added with gentle agitation to make a concentration of 4% solids in solution.

Coating of Substrate Particles with Hydroxypropyl Cellulose Coating Solution:
3. 6000 g of maltitol was added to a fluid bed, top spray granulator.
4. The Lossy Coating solution was sprayed onto the Mannitol at an approximate average spray rate of 103 g/minute to make a 1.0% (w/w) lossy coated particle to a target end of spray percent moisture as noted in Table 9A as measured by loss on drying.
5. The lossy coated particles were then further dried to percent moisture as recorded in Table 9A.

Examples 6A-G: Production of Lossy Coated Particles Using 40,000 Daltons MW 1% Hydroxypropylcellulose as Activator The lossy coated particle was prepared utilizing the procedure in Example 6, utilizing 1.0% weight gain of Hydroxypropylcellulose. The lossy coated particles were blended with coated APAP (90% potency) to a concentration of 20%, 30%, 40%, or 50% to make 80, 160 or 325 mg acetaminophen dose tablets (see Tables 9A and 9B).

TABLE 9A

| Material/Output | Example 6 | Example 6A | Example 6B | Example 6C |
|---|---|---|---|---|
| Comment | Lossy coated particles alone | Blended with APAP Particles | Blended with APAP Particles | Blended with APAP Particles |
| Substrate | Maltitol | Maltitol | Maltitol | Maltitol |
| Activator | HPC | HPC | HPC | HPC |
| Activator Concentration (% w/w) | 1.0 | 1.0 | 1.0 | 1.0 |
| Average Molecular Weight of Polymer (×1000 Daltons) | 40 | 40 | 40 | 40 |
| Pharmaceutically Active Agent | N/A | APAP | APAP | APAP |
| Active Dose per tablet | N/A | 80 | 80 | 160 |
| % Lossy Coated Particles in Powder Blend | N/A | 20 | 30 | 30 |
| % Moisture at End of Spraying | 2.4 | N/A | N/A | N/A |
| % Moisture of Lossy Coated Particles Before Sintering | 1.6 | 1.1 | 0.87 | 0.87 |
| e' | 1.8016 | 1.7847 | 1.7619 | 1.7619 |
| e" | 0.0157 | 0.0140 | 0.0121 | 0.0121 |
| Q value | 115 | 127 | 146 | 146 |
| Lossy Coated Particle Geometric Mean Diameter (μm) | 305 | N/A | N/A | N/A |
| Tablet Diameter (mm) | 12.5 | 12.5 | 12.5 | 12.5 |
| Tablet Weight (mg) | N/A | 444 | 296 | 593 |
| Tablet Thickness (mm) | N/A | 3.58 | 2.58 | 4.74 |
| Tablet Density (g/cc) | N/A | 1.0 | 0.9 | 1.0 |
| Sintering Time (sec) | N/A | 1.0 | 0.5 | 1.0 |
| Oral Disintegration Time (sec) | N/A | 11 | 9 | 13 |
| Hardness | N/A | 0.33 | N/A | N/A |
| Friability % (15 drops) | N/A | 0.5 | 0.3 | 0.5 |
| Friability % (100 drops) | N/A | 1.0 | 0.9 | N/A |

TABLE 9B

| Material/Output | Example 6D | Example 6E | Example 6F | Example 6G |
|---|---|---|---|---|
| Comment | Blended with APAP Particles | Blended with APAP Particles | Blended with APAP Particles | Blended with APAP Particles |
| Substrate | Maltitol | Maltitol | Maltitol | Maltitol |
| Activator | HPC | HPC | HPC | HPC |
| Activator Concentration (% w/w) | 1.0 | 1.0 | 1.0 | 1.0 |
| Average Molecular Weight of Polymer (×1000 Daltons) | 40 | 40 | 40 | 40 |
| Pharmaceutically Active Agent | APAP | APAP | APAP | APAP |
| Active Dose per tablet | 160 | 325 | 160 | 325 |
| % Lossy Coated Particles in Powder Blend | 40 | 40 | 50 | 50 |
| % Moisture at End of Spraying | N/A | N/A | N/A | N/A |
| % Moisture of Lossy Coated Particles Before Sintering | 0.73 | 0.73 | 0.58 | 0.58 |
| e' | 1.7551 | 1.7551 | 1.7471 | 1.7471 |
| e" | 0.0107 | 0.0107 | 0.0099 | 0.0099 |
| Q value | 164 | 164 | 176 | 176 |
| Lossy Coated Particle Geometric Mean Diameter (μm) | N/A | N/A | N/A | N/A |
| Tablet Diameter (mm) | 12.5 | 12.5 | 12.5 | 12.5 |
| Tablet Weight (mg) | 444 | 1000 | 356 | 722 |
| Tablet Thickness (mm) | 3.71 | 7.74 | 3.26 | 5.91 |
| Tablet Density (g/cc) | 0.9 | 1.0 | 0.9 | 1.0 |
| Sintering Time (sec) | 1.0 | 1.5 | 1.5 | 1.5 |
| Oral Disintegration Time (sec) | 6 | N/A | 9 | N/A |
| Hardness | N/A | N/A | N/A | N/A |

TABLE 9B-continued

| Material/Output | Example 6D | Example 6E | Example 6F | Example 6G |
| --- | --- | --- | --- | --- |
| Friability % (15 drops) | 0.9 | Broke | 1.5 | broke |
| Friability % (100 drops) | N/A | N/A | N/A | N/A |

Examples 7: Production of Lossy Coated Particles Using 140,000 Daltons MW, 1% Hydroxypropyl Cellulose A batch of 6.1 kg of lossy maltitol particles was prepared according to the procedure below. The lossy coated particles were dielectrically characterized using a Slotted line method and reported in Tables 10A. These lossy coated particles were then used to produce the orally disintegrating tablets in Examples 7A-G (Tables 10A and 10B).

Lossy Coating Solution:
1. Purified Water USP added to a suitably sized stainless steel container.
2. 60 g of hydroxypropylcellulose (commercially available as Klucel® JF from Ashland Specialty Ingredients), as an activator, was added with gentle agitation to make a concentration of 4% solids in solution.

Coating of Substrate Particles with Hydroxypropylcellulose Coating Solution:
3. 6000 g of maltitol was added to a fluid bed, top spray granulator.
4. The Lossy Coating Solution was sprayed onto the Mannitol at an approximate average spray rate of 111 g/minute to make a 1.0% (w/w) lossy coated particle to a target end of spray percent moisture as noted in Table 10A as measured by loss on drying.
5. The granules were then further dried to percent moisture as recorded in Table 10A.

Examples 7A-G: Production of Lossy Coated Particles Using 140,000 Daltons, 1% Hydroxypropyl Cellulose as Activator The lossy coated particles were prepared utilizing the procedure in Example 7, utilizing 1.0% of weight gain of Hydroxypropylcellulose. The lossy coated particles were blended with coated APAP (90% potency) to a concentration of 20%, 30%, 40%, or 50% to make 80, 160 or 325 mg acetaminophen dose tablets (see Tables 10A and 10B).

TABLE 10A

| Material/Output | Example 7 | Example 7A | Example 7B | Example 7C |
| --- | --- | --- | --- | --- |
| Comment | Lossy coated particles alone | Blended with APAP Particles | Blended with APAP Particles | Blended with APAP Particles |
| Substrate | Maltitol | Maltitol | Maltitol | Maltitol |
| Activator | HPC | HPC | HPC | HPC |
| Activator Concentration (% w/w) | 1.0 | 1.0 | 1.0 | 1.0 |
| Average Molecular Weight of Polymer (×1000 Daltons) | 140 | 140 | 140 | 140 |
| Pharmaceutically Active Agent | None | APAP | APAP | APAP |
| Active Dose per tablet | N/A | 80 | 80 | 160 |
| % Lossy Coated Particles in Powder Blend | N/A | 20 | 30 | 30 |
| % Moisture at End of Spraying | 3.1 | N/A | N/A | N/A |
| % Moisture of Lossy Coated Particles Before Sintering | 1.0 | 0.7 | 0.7 | 0.8 |
| e' | 1.8073 | 1.7533 | 1.7504 | 1.7504 |
| e" | 0.0149 | 0.0122 | 0.0108 | 0.0108 |
| Q value | 121 | 144 | 162 | 162 |
| Lossy Coated Particle Geometric Mean Diameter (μm) | 338 | N/A | N/A | N/A |
| Tablet Diameter (mm) | 12.5 | 12.5 | 12.5 | 12.5 |
| Tablet Weight (mg) | N/A | 444 | 296 | 593 |
| Tablet Thickness (mm) | N/A | 3.94 | 2.60 | 4.95 |
| Tablet Density (g/cc) | N/A | 0.9 | 0.9 | 0.9 |
| Sintering Time (sec) | N/A | 0.5 | 0.5 | 1.0 |
| Oral Disintegration Time (sec) | N/A | 8 | 9 | 12 |
| Hardness | N/A | N/A | 0.53 | 0.33 |
| Friability % (15 drops) | N/A | 0.5 | 0.5 | 0.8 |
| Friability % (100 drops) | N/A | 2.5 | Broke | 7.1 |

TABLE 10B

| Material/Output | Example 7D | Example 7E | Example 7F | Example 7G |
|---|---|---|---|---|
| Comment | Blended with APAP Particles | Blended with APAP Particles | Blended with APAP Particles | Blended with APAP Particles |
| Substrate | Maltitol | Maltitol | Maltitol | Maltitol |
| Activator | HPC | HPC | HPC | HPC |
| Activator Concentration (% w/w) | 1.0 | 1.0 | 1.0 | 1.0 |
| Average Molecular Weight of Polymer (×1000 Daltons) | 140 | 140 | 140 | 140 |
| Pharmaceutically Active Agent | APAP | APAP | APAP | APAP |
| Active Dose per tablet | 160 | 325 | 160 | 325 |
| % Lossy Coated Particles in Powder Blend | 40 | 40 | 50 | 50 |
| % Moisture at End of Spraying | N/A | N/A | N/A | N/A |
| % Moisture of Lossy Coated Particles Before Sintering | 0.5 | 0.5 | 0.5 | 0.3 |
| e' | 1.7397 | 1.7397 | 1.7368 | 1.7368 |
| e" | 0.0087 | 0.0087 | 0.0085 | 0.0085 |
| Q value | 200 | 200 | 204 | 204 |
| Lossy Coated Particle Geometric Mean Diameter (μm) | N/A | N/A | N/A | N/A |
| Tablet Diameter (mm) | 12.5 | 12.5 | 12.5 | 12.5 |
| Tablet Weight (mg) | 444 | 1000 | 356 | 722 |
| Tablet Thickness (mm) | 3.97 | 7.97 | 3.28 | 5.97 |
| Tablet Density (g/cc) | 0.9 | 1.0 | 0.9 | 1.0 |
| Sintering Time (sec) | 1.0 | 1.5 | 1.5 | 1.5 |
| Oral Disintegration Time (sec) | 8 | 16 | 9 | N/A |
| Hardness | 0.85 | 0.65 | 0.31 | 0.41 |
| Friability % (15 drops) | 0.8 | 0.8 | 2.9 | broke |
| Friability % (100 drops) | Broke | N/A | N/A | N/A |

Examples 8: Production of Lossy Coated Particles Using 0.5% Hydroxyethyl Cellulose as Activator A batch of 6.1 kg of lossy coated maltitol particles was prepared according to the procedure below. The lossy coated particles were dielectrically characterized using the Slotted line method and reported in Table 11. These lossy coated particles were then used to produce the orally disintegrating tablets in Examples 8A-D (Table 11).

Polymer Coating Solution:
1. Purified Water USP added to a suitably sized stainless steel container.
2. 60 g of hydroxyethyl cellulose (commercially available as Natrosol 250L from Ashland Specialty Ingredients), as an activator, was added with gentle agitation to make a concentration of 2% solids in solution.

Coating of Substrate Particles with Hydroxyethyl Cellulose Coating Solution:
3. 6000 g of maltitol was added to a fluid bed, top spray granulator.
4. The Polymer Coating solution was sprayed onto the Mannitol at an approximate average spray rate of 111 g/minute to make a 0.5% (w/w) lossy coated particle to a target end of spray percent moisture as noted in Table 11 as measured by loss on drying.
5. The granules were then further dried to percent moisture as recorded in Table 11.

Examples 8A-D

The lossy coated particles were prepared utilizing the procedure in Example 8, utilizing 1.0% weight gain of Hydroxyethyl cellulose. The lossy coated particles were blended with coated APAP (90% potency) to a concentration of 20%, 30%, 40%, or 50% to make 80, 160 or 325 mg acetaminophen dose tablets (see Table 11).

TABLE 11

| Material/Output | Example 8 | Example 8A | Example 8B | Example 8C | Example 8D |
|---|---|---|---|---|---|
| Comment | Lossy coated particles alone | Blended with APAP Particles | Blended with APAP Particles | Blended with APAP Particles | Blended with APAP Particles |
| Substrate | Maltitol | Maltitol | Maltitol | Maltitol | Maltitol |
| Activator | HEC | HEC | HEC | HEC | HEC |
| Activator Concentration (% w/w) | 0.5 | 0.5 | 0.5 | 0.5 | 0.5 |
| Average Molecular Weight of Polymer (×1000 Daltons) | 75 | 75 | 75 | 75 | 75 |
| Pharmaceutically Active Agent | None | APAP | APAP | APAP | APAP |
| Active Dose per tablet | N/A | 80 | 80 | 160 | 160 |
| % Lossy Coated Particles in Powder Blend | N/A | 20 | 30 | 30 | 40 |
| % Moisture at End of Spraying | 2.7 | N/A | N/A | N/A | N/A |
| % Moisture of Lossy Coated Particles Before Sintering | 1.3 | 0.8 | 0.6 | 0.6 | 0.4 |
| e' | 1.8065 | 1.7854 | 1.7741 | 1.7741 | 1.7743 |
| e" | 0.0275 | 0.0197 | 0.0159 | 0.0159 | 0.0130 |
| Q value | 66 | 91 | 112 | 112 | 136 |
| Tablet Diameter (mm) | N/A | 12.5 | 12.5 | 12.5 | 12.5 |
| Tablet Weight (mg) | N/A | 444 | 296 | 593 | 444 |
| Tablet Thickness (mm) | N/A | 4.07 | 2.86 | 4.74 | 4.05 |
| Tablet Density (g/cc) | N/A | 0.9 | 0.8 | 0.9 | 0.9 |
| Sintering Time (sec) | N/A | 0.5 | 0.5 | 0.5 | 1.5 |

TABLE 11-continued

| Material/Output | Example 8 | Example 8A | Example 8B | Example 8C | Example 8D |
|---|---|---|---|---|---|
| Oral Disintegration Time (sec) | N/A | 9 | 5 | 8 | 9 |
| Hardness | N/A | 0.36 | 0.61 | 0.30 | 0.85 |
| Friability % (15 drops) | N/A | 0.51 | 1.2 | 0.9 | 2.9 |
| Friability % (100 drops) | N/A | N/A | N/A | N/A | N/A |

Examples 9: Production of Lossy Coated Particles Using 1% Hydroxyethyl Cellulose as Activator A batch of 6.1 kg of lossy coated maltitol particles was prepared according to the procedure below. The lossy coated particles were dielectrically characterized using the Slotted line method and reported in Table 12. These lossy coated particles were then used to produce the orally disintegrating tablets in Examples 9A-D (Table 12).

Lossy Coating Solution:
1. Purified Water USP added to a suitably sized stainless steel container.
2. 120 g of hydroxyethyl cellulose (commercially available as Natrosol 250L from Ashland Specialty Ingredients), as the activator, was added with gentle agitation to make a concentration of 4% solids in solution.

Coating of Substrate Particles with Hydroxyethyl Cellulose Coating Solution:
3. 6000 g of maltitol was added to a fluid bed, top spray granulator.
4. The Lossy Coating Solution was sprayed onto the Mannitol at an approximate average spray rate of 111 g/minute to make a 1.0% (w/w) lossy coated particle to a target end of spray percent moisture as noted in Table 12.
5. The granules were then further dried to percent moisture as recorded in Table 12.

Examples 9A-D

The lossy coated particles were prepared utilizing the procedure in Example 9, utilizing 0.5% weight gain of Hydroxyethyl cellulose. The lossy coated particles were blended with coated APAP (90% potency) to a concentration of 20%, 30%, 40%, or 50% to make 80, 160 or 325 mg acetaminophen dose tablets (see Table 12).

TABLE 12

| Material/Output | Example 9 | Example 9A | Example 9B | Example 9C | Example 9D |
|---|---|---|---|---|---|
| Comment | Lossy coated particles alone | Blended with APAP Particles | Blended with APAP Particles | Blended with APAP Particles | Blended with APAP Particles |
| Substrate | Maltitol | Maltitol | Maltitol | Maltitol | Maltitol |
| Activator | HEC | HEC | HEC | HEC | HEC |
| Activator Concentration (% w/w) | 1.0 | 1.0 | 1.0 | 1.0 | 1.0 |
| Average Molecular Weight of Polymer (×1000 Daltons) | 75 | 75 | 75 | 75 | 75 |
| Pharmaceutically Active Agent | None | APAP | APAP | APAP | APAP |
| Active Dose per tablet | N/A | 80 | 80 | 160 | 160 |
| % Lossy Coated Particles in Powder Blend | N/A | 20 | 30 | 30 | 40 |
| % Moisture at End of Spraying | 2.2 | N/A | N/A | N/A | N/A |
| % Moisture of Lossy Coated Particles Before Sintering | 1.3 | 0.7 | 0.6 | 0.6 | 0.5 |
| e' | 1.7532 | 1.7411 | 1.7444 | 1.7444 | 1.7495 |
| e" | 0.0378 | 0.0277 | 0.0250 | 0.0250 | 0.0202 |
| Q value | 46 | 63 | 70 | 70 | 87 |
| Tablet Diameter (mm) | N/A | 12.5 | 12.5 | 12.5 | 12.5 |
| Tablet Weight (mg) | N/A | 444 | 296 | 593 | 444 |
| Tablet Thickness (mm) | N/A | 4.13 | 2.68 | 5.23 | 4.13 |
| Tablet Density (g/cc) | N/A | 0.8 | 0.9 | 0.9 | 0.8 |
| Sintering Time (sec) | N/A | 0.5 | 0.5 | 0.5 | 1.0 |
| Oral Disintegration Time (sec) | N/A | 19 | 8 | 19 | 8 |
| Hardness | N/A | 0.43 | 0.67 | 0.52 | 0.60 |
| Friability % (15 drops) | N/A | 2.3 | 0.9 | 2.5 | 2.7 |
| Friability % (100 drops) | N/A | N/A | N/A | N/A | N/A |

Examples 10: Production of Lossy Coated Particles Using 2% Hydroxypropyl Cellulose as Activator A batch of 6.1 kg of lossy coated maltitol particles was prepared according to the procedure below. The lossy coated particles were dielectrically characterized in using the Slotted line method and reported in Table 13. These lossy coated particles were then used to produce the orally disintegrating tablets in Examples 10A-D (Table 13).

Examples 10A-F

The lossy coated particles were prepared utilizing the procedure in Example 10, utilizing 1.0% weight gain of Hydroxyethyl cellulose. The lossy coated particles were blended with coated APAP (90% potency) to a concentration of 20%, 30%, 40%, or 50% to make 80, 160 or 325 mg acetaminophen dose tablets (see Tables 13).

TABLE 13

| Material/Output | Example 10 | Example 10A | Example 10B | Example 10C | Example 10D | Example 10E | Example 10F |
|---|---|---|---|---|---|---|---|
| Comment | Lossy coated particles alone | Blended with APAP Particles | Blended with APAP Particles | Blended with APAP Particles | Blended with APAP Particles | Blended with APAP Particles | Blended with APAP Particles |
| Substrate | Maltitol | Maltitol | Maltitol | Maltitol | Maltitol | Maltitol | Maltitol |
| Activator | HPC | HPC | HPC | HPC | HPC | HPC | HPC |
| Activator Concentration (% w/w) | 2.0 | 2.0 | 2.0 | 2.0 | 2.0 | 2.0 | 2.0 |
| Average Molecular Weight of Polymer (×1000 Daltons) | 80 | 80 | 80 | 80 | 80 | 80 | 80 |
| Pharmaceutically Active Agent | None | APAP | APAP | APAP | APAP | APAP | APAP |
| Active Dose per tablet | N/A | 80 | 80 | 160 | 160 | 325 | 160 |
| % Lossy Coated Particles in Powder Blend | N/A | 20 | 30 | 30 | 40 | 40 | 50 |
| % Moisture at End of Spraying | 3.4 | N/A | N/A | N/A | N/A | N/A | N/A |
| % Moisture of Lossy Coated Particles Before Sintering | 1.5 | 1.1 | 0.9 | 0.7 | 0.7 | 0.7 | 0.6 |
| e' | 1.8140 | 1.7847 | 1.7792 | 1.7792 | 1.7554 | 1.7554 | 1.7601 |
| e" | 0.0214 | 0.0129 | 0.0099 | 0.0099 | 0.0084 | 0.0084 | 0.0066 |
| Q value | 85 | 138 | 180 | 180 | 209 | 209 | 267 |
| Tablet Diameter (mm) | N/A | 12.5 | 12.5 | 12.5 | 12.5 | 12.5 | 12.5 |
| Tablet Weight (mg) | N/A | 444 | 296 | 593 | 444 | 1000 | 356 |
| Tablet Thickness (mm) | N/A | 3.49 | 2.67 | 4.74 | 3.77 | 8.17 | 3.25 |
| Tablet Density (g/cc) | N/A | 1.0 | 0.87 | 0.99 | 0.93 | 0.97 | 0.86 |
| Sintering Time (sec) | N/A | 0.5 | 0.5 | 0.5 | 0.5 | 0.5 | 0.5 |
| Oral Disintegration Time (sec) | N/A | 10 | 8 | 11 | 14 | 18 | 8 |
| Friability % (15 drops) | N/A | 0.50 | 0.60 | 0.60 | 0.53 | 2.24 | 1.21 |
| Friability % (100 drops) | N/A | 1.1 | N/A | N/A | N/A | N/A | N/A |

Lossy Coating Solution:
1. Purified Water USP added to a suitably sized stainless steel container.
2. 120 g of hydroxypropyl cellulose (commercially available as Klucel® EF from Ashland Specialty Ingredients), as an activator, was added with gentle agitation to make a concentration of 4% solids in solution.

Coating of Substrate Particles with Hydroxyethyl cellulose Coating Solution:
3. 6000 g of maltitol was added to a fluid bed, top spray granulator.
4. The Lossy Coating Solution was sprayed onto the Mannitol at an approximate average spray rate of 110 g/minute to make a 2% (w/w) lossy coated particle to a target end of spray percent moisture as noted in Table 13 as measured by loss on drying.
5. The granules were then dried to percent moisture as recorded in Table 13.

Examples 11: Production of Lossy Coated Particles Using 0-1% Hydroxyethyl Cellulose as Activator; Combined with Sodium Citrate and/or Glycerin as Adjuvants A batch of 6.1 kg of lossy coated maltitol particles was prepared according to the procedure below. The lossy coated particles were dielectrically characterized in using the Slotted line method and reported in Table 14. These lossy coated particles were then used to produce the orally disintegrating tablets in Examples 11A-E (Tables 14A-14B). Samples 11F and 11G were made as comparator blends with uncoated maltitol to demonstrate tablet samples without coated particles. These comparator blends did not sinter to form tablets.

Lossy Coating Solution:
1. Purified Water USP added to a suitably sized stainless steel container.
2. 120 g of hydroxyethyl cellulose (commercially available as Natrosol® 250L), as an activator, was added with gentle agitation to make a concentration of 2.5-4% solids in solution (approximately 25 kg).

Coating of Substrate Particles with Hydroxyethyl Cellulose Coating Solution:

3. 6000 g of maltitol was added to a fluid bed, top spray granulator.
4. The Lossy Coating Solution was sprayed onto the Maltitol at an approximate average spray rate of 110 g/minute to make a 2% (w/w) lossy coated particle to a target end of spray percent moisture as noted in Tables 14A-14B as measured by loss on drying.
5. The granules were then dried to percent moisture as recorded in Tables 14A-14B.

Examples 11, 11A-E

The lossy coated particles were prepared utilizing the procedure in Example 11, utilizing 1.0% weight gain of Hydroxyethyl cellulose. The lossy coated particles were blended with coated APAP (90% potency) to a concentration of 20%, 30%, 40%, or 50% to make 80, 160 or 325 mg acetaminophen dose tablets (see Tables 14A and 14B).

TABLE 14A

| Material/Output | Example 11 | Example 11A | Example 11B | Example 11C |
|---|---|---|---|---|
| Comment | 1% HEC on Maltitol | 1% HEC with 1% Glycerin on Maltitol | 1% HEC with 1% Glycerin and 1% Sodium Citrate on Maltitol | 1% HEC with 2% Glycerin and 0.5% Sodium Citrate on Maltitol |
| Substrate | Maltitol | Maltitol | Maltitol | Maltitol |
| Activator | HEC | HEC | HEC | HEC |
| Activator Concentration (% w/w) | 1.0 | 1.0 | 1.0 | 1.0 |
| Average Molecular Weight of Polymer (×1000 Daltons) | 80 | 80 | 80 | 80 |
| Pharmaceutically Active Agent | APAP | APAP | APAP | APAP |
| Active Dose per tablet | 160 mg | 160 mg | 160 mg | 160 mg |
| % Lossy Coated Particles in Powder Blend | 71.45 | 71.45 | 71.45 | 71.45 |
| % Moisture at End of Spraying | 3.00 | 1.89 | 1.78 | 1.79 |
| % Moisture of Lossy Coated Particles Before Sintering | 0.88 | 0.78 | 1.14 | 0.77 |
| e' | 0.8093 | 1.8385 | 1.7756 | — |
| e" | 0.0408 | 0.0312 | 0.0756 | — |
| Q value | 44 | 59 | 23 | — |
| Tablet Diameter (mm) | 12.5 | 12.5 | 12.5 | 12.5 |
| Tablet Weight (mg) | 600 | 600 | 600 | 600 |
| Tablet Thickness (mm) | 5.25 | 5.25 | 5.44 | 5.44 |
| Tablet Density (g/cc) | 0.644 | 0.644 | 0.668 | 0.668 |
| Sintering Time (sec) | 1 | 1 | 1 | 1 |
| Oral Disintegration Time (sec) | 11 | 14.7 | 10.7 | 11.5 |
| Friability % (15 drops) | N/A | 0.50 | 0.60 | 0.60 |
| Friability % (100 drops) | N/A | N/A | N/A | N/A |

HEC: Hydroxyethyl cellulose

TABLE 14B

| Material/Output | Example 11D | Example 11E | Example 11F | Example 11G |
|---|---|---|---|---|
| Comment | 1% HEC with 3% Glycerin on Maltitol | 1% HEC with 3% Glycerin and 1% Sodium Citrate on Maltitol | 0% HEC with 1% Glycerin on Maltitol | 0% HEC with 3% Glycerin on Maltitol |
| Substrate | Maltitol | Maltitol | Maltitol | Maltitol |
| Activator | HEC | HEC | None | None |
| Activator Concentration (% w/w) | 1.0 | 1.0 | 0.0 | 0.0 |
| Average Molecular Weight of Polymer (×1000 Daltons) | 80 | 80 | N/A | N/A |
| Pharmaceutically Active Agent | APAP | APAP | APAP | APAP |
| Active Dose per tablet | 160 mg | 160 mg | 160 mg | 160 mg |
| % Lossy Coated Particles in Powder Blend | 71.45 | 71.45 | 71.45[a] | 71.45[a] |
| % Moisture at End of Spraying | 1.75 | 2.03 | 1.54 | 1.87 |
| % Moisture of Lossy Coated Particles Before Sintering | 0.78 | 1.12 | 0.53 | 0.81 |
| e' | 1.8463 | 1.8320 | — | — |
| e" | 0.0333 | 0.0914 | — | — |
| Q value | 55 | 20 | — | — |
| Tablet Diameter (mm) | 12.5 | 12.5 | 12.5 | 12.5 |
| Tablet Weight (mg) | 600 | 600 | 600 | 600 |
| Tablet Thickness (mm) | 5.25 | 5.25 | 5.25 | 5.25 |
| Tablet Density (g/cc) | 0.644 | 0.644 | 0.644 | 0.644 |
| Sintering Time (sec) | 1 | 1 | 1 | 1 |
| Oral Disintegration Time (sec) | 18.5 | 9.3 | N/A[b] | N/A[b] |
| Friability % (15 drops) | 0.53 | 2.24 | Failed[b] | Failed[b] |
| Friability % (100 drops) | N/A | N/A | N/A | N/A |

HEC: Hydroxyethyl cellulose
[a] particles without HEC
[b] could not be tested since these blends did not sinter to form a tablet
e' and e" tested on coated particles Examples 12: Production of Lossy Coated Particles Using Various Polymers as Activators Batches of 6.1 kg of lossy coated maltitol particles was prepared according to the procedure below. The lossy coated particles were dielectrically characterized in using the Slotted line method and reported in Tables 15A and 15B. These lossy coated particles were then used to produce the orally disintegrating tablets in Examples 12 and 12A-12H (Tables 15A and 15B).

Lossy Coating Solution:
1. Purified Water USP added to a suitably sized stainless steel container.
2. 120 g of a polymer (as shown in the Table 15 below) as an activator, was added with gentle agitation to make a concentration of 2-5% solids in solution, depending on the polymer being evaluated (approximately 25 kg).

Coating of Substrate Particles with Polymer Coating Solution:
3. 6000 g of maltitol was added to a fluid bed, top spray granulator.
4. The Lossy Coating Solution was sprayed onto the Maltitol at an approximate average spray rate of approximately 100-110 g/minute to make a 1% (w/w) lossy coated particle to a target end of spray percent moisture as noted in Tables 15A and 15B as measured by loss on drying.

5. The granules were then dried.

Examples 12, 12A-H

The lossy coated particles were prepared utilizing the procedure in Example 12, utilizing 1.0% weight gain of a polymer.

TABLE 15A

| Material/ Output | Example 12 | Example 12A | Example 12B | Example 12C | Example 12D |
|---|---|---|---|---|---|
| Comment | 1% Polyvinyl Alcohol[1] on Maltitol | 1% Polyvinyl Alcohol-Polyethylene Glycol Graft Co-Polymer "IR"[2] on Maltitol | 1% Polyvinyl Alcohol-Polyethylene Glycol Graft Co-Polymer[3] on Maltitol | 1% Polyvinyl Alcohol-Polyethylene Glycol Graft Co-Polymer[3] on Maltitol | 1% Polyvinyl Acetate[4] on Maltitol |
| Substrate | Maltitol | Maltitol | Maltitol | Maltitol | Maltitol |
| Activator | Polyvinyl Alcohol | Kollicoat ® IR | Kollicoat ® Protect | Kollicoat ® Protect | Kollicoat ® SR30 |
| Activator Concentration (% w/w) | 1.0 | 1.0 | 1.0 | 1.0 | 1.0 |
| Pharmaceutical Active Agent | N/A | N/A | N/A | N/A | N/A |
| Active Dose per tablet | N/A | N/A | N/A | N/A | N/A |
| % Lossy Coated Particles in Powder Blend | 100.0 | 100.0 | 100.0 | 100.0 | 100.0 |
| % Moisture of Lossy Coated Particles Before Sintering | 0.76 | 1.33 | 1.03 | 1.03 | 1.46 |
| e' | 1.7203 | 1.8520 | 1.7746 | 1.7746 | 1.8796 |
| e" | 0.1071 | 0.0189 | 0.0414 | 0.0414 | 0.0938 |
| Q value | 16 | 98 | 43 | 43 | 20 |
| Tablet Diameter (mm) | 12.5 | 12.5 | 12.5 | 12.5 | 12.5 |
| Tablet Weight (mg) | 600 | 600 | 600 | 600 | 600 |
| Sintering Time (sec) | 1 | 1 | 1 | 1 | 1 |
| Oral Disintegration Time (sec) | 4-5 | 5-9 | 3-5 | n/a | 9-13 |
| Friability % (15 drops) | 0.83-2.73 | 0.28-2.78 | 2.0-3.9 | Too soft to test | 0.51-1.91 | e' and e" tested on coated particles
[1] Available as Emprove ® from EMD Millipore Corporation
[2] Available as Kollicoat IR ® ® from the BASF Corporation
[3] Available as Kollicoat Protect ® from the BASF Corporation
[4] Available as Kollicoat SR30 ® from the BASF Corporation

TABLE 15B

| Material/ Output | Example 12E | Example 12F | Example 12G | Example 12H |
|---|---|---|---|---|
| Comment | 1% Copolymer of ethyl acrylate, methyl methacrylate[5] on Maltitol | 1% Povidone[6] (Plasdone) on Maltitol | 1% Polyvinyl caprolactam - polyvinyl acetate - polyethylene glycol graft copolymer[7] Maltitol | 1% Copolymer of N-vinyl-2-pyrrolidone and vinyl acetate[8] on Maltitol |
| Substrate | Maltitol | Maltitol | Maltitol | Maltitol |
| Activator | Eudragit ®RS30D | Plasdone ® K12 | SoluPlus ® | Plasdone ® S630 |
| Activator Concentration (% w/w) | 1.0 | 1.0 | 1.0 | 1.0 |
| Pharmaceutical Active Agent | N/A | N/A | N/A | N/A |
| Active Dose per tablet | N/A | N/A | N/A | N/A |
| % Lossy Coated Particles in Powder Blend | 100.0 | 100.0 | 100.0 | 100.0 |
| % Moisture of Lossy Coated Particles Before Sintering | 1.14 | 1.13 | 1.27 | 1.36 |
| e' | 1.6016 | — | 1.7686 | 1.8605 |
| e" | 0.1133 | — | 0.0731 | 0.0332 |
| Q value | 14 | — | 24 | 56 |

TABLE 15B-continued

| Material/ Output | Example 12E | Example 12F | Example 12G | Example 12H |
|---|---|---|---|---|
| Tablet Diameter (mm) | 12.5 | 12.5 | 12.5 | 12.5 |
| Tablet Weight (mg) | 600 | 600 | 600 | 600 |
| Sintering Time (sec) | 1 | 1 | 1 | 1 |
| Oral Disintegration Time (sec) | 13-22 | 4-5 | 5-11 | 2-3 |
| Friability % (15 drops) | 0.71-2.00 | 3.7 | 0.7-4.7 | 1.5-3.7 | e' and e" tested on coated particles
[5]Available as Eudragit ® RS30D from the Evonik Corporation
[6]Available as Plasdone ® K12 from the Ashland Corporation
[7]Available as Soluplus ® from the BASF Corporation
[8]Available as Plasdone ® S630 from the Ashland Corporation

Example 13: Preparation of Eudragit RD30D Coated Particle Blended with Encapsulated Acetaminophen The batch from Example 12D above was also blended with 29% coated acetaminophen and sintered with radiofrequency energy to produce tablets, as outlined in Example 12. Various parameters for such particles are set forth below.

TABLE 16

| Sample | LOD[1] | e' | e" | Q | Friability (%) 15 drops | Oral Disintegration (sec) |
|---|---|---|---|---|---|---|
| Eudragit RS30D Coated Particles with Encapsulated APAP | 0.726 | 1.6219 | 0.1243 | 13 | 0.39-0.77 | 5-10 |

[1]Loss on Drying (% water by weight)

Example 14: Production of Lossy Coated Particles Using Various Polymers with Activators with Plasticizers Batches of 6.1 kg of lossy coated maltitol particles was prepared according to the procedure below. The lossy coated particles were dielectrically characterized in using the Slotted line method and reported in Table 17A. These lossy coated particles were then used to produce the orally disintegrating tablets in Examples 14A-H (Tables 17A-17B).

Lossy Coating Solution:
1. Purified Water USP added to a suitably sized stainless steel container.
2. 120 g of a polymer (as shown in the Table below) as an activator and 47 g of plasticizer (ratio of 72:24 of activator: plasticizer) was added with gentle agitation to make a concentration of 2-5% solids in solution, depending on the polymer being evaluated.

Coating of Substrate Particles with Polymer Coating Solution:
3. 6000 g of maltitol was added to a fluid bed, top spray granulator.
4. The Lossy Coating Solution was sprayed onto the Maltitol at an approximate average spray rate of approximately 100-110 g/minute to make a 1-2% (w/w) lossy coated particle to a target end of spray percent moisture as noted in Tables 17A-17B as measured by loss on drying.
5. The granules were then dried.

Examples 14, 14A-H

The lossy coated particles were prepared utilizing the procedure in Example 14, utilizing 1.0% weight gain of polymer (depending on type in Tables 17A-17B).

TABLE 17A

| Material/ Output | Example 14 | Example 14A | Example 14B | Example 14C | Example 14D |
|---|---|---|---|---|---|
| Comment | 2% Eudragit RL30D[1] with DBS$^a$ on Maltitol | 1% Eudragit RL30D with DBS$^a$ on Maltitol | 2% Eudragit RS30D[2] with DBS$^a$ on Maltitol | 2% Eudragit RS30D[2] with DBS$^a$ on Maltitol | 1% Eudragit RS30D[2] with DBS$^a$ on Maltitol |
| Substrate | Maltitol | Maltitol | Maltitol | Maltitol | Maltitol |
| Activator | Eudragit ® RL30D | Eudragit ® RL30D | Eudragit ® RS30D | Eudragit ® RS30D | Eudragit ® RS30D |
| Activator Concentration (% w/w) | 2.0 | 1.0 | 1.0 | 1.0 | 1.0 |
| Pharmaceutical Active Agent | N/A | N/A | N/A | N/A | N/A |
| Active Dose per tablet | N/A | N/A | N/A | N/A | N/A |
| % Lossy Coated Particles in Powder Blend | 100.0 | 100.0 | 100.0 | 100.0 | 100.0 |
| % Moisture of Lossy Coated Particles Before Sintering | 0.089 | 0.119 | 0.026 | 0.026 | 0.019 |

TABLE 17A-continued

| Material/ Output | Example 14 | Example 14A | Example 14B | Example 14C | Example 14D |
|---|---|---|---|---|---|
| e' | 1.6623 | 1.7003 | 1.6604 | 1.6604 | 1.6467 |
| e" | 0.0256 | 0.0665 | 0.0179 | 0.0179 | 0.0437 |
| Q value | 65 | n/a | 93 | 93 | 38 |
| Tablet Diameter (mm) | 12.5 | 12.5 | 12.5 | 12.5 | 12.5 |
| Tablet Weight (mg) | 600 | 600 | 600 | 600 | 600 |
| Sintering Time (sec) | 1 | 1 | 1 | 1 | 1 |
| Oral Disintegration Time (sec) | NR | NR | NR | NR | NR |
| Friability % (15 drops) | 5.2 | Could not make tablets | Failed at 7 drops | 4.1-4.5 | Could not make tablets | e' and e" tested on coated particles
[a]DBS: Dibuytl Sebecate (plasticizer)
b: PG: Propylene Glycol (plasticizer)
NR—not recorded
[1]Eudragit ® RL30D from Evonik Corporation is copolymer of ethyl acrylate, methyl methacrylate and a low content of methacrylic acid ester with quaternary ammonium groups
[2]Eudragit ® RS30D from Evonik Corporation is a copolymer of ethyl acrylate, methyl methacrylate and a low content of methacrylic acid ester with quaternary ammonium groups

TABLE 17B

| Material/ Output | Example 14E | Example 14F | Example 14G | Example 14H |
|---|---|---|---|---|
| Comment | 2% Polyvinyl Alcohol-Polyethylene Glycol Graft Co-Polymer[3] and PG[b] on Maltitol | 1% Polyvinyl Alcohol-Polyethylene Glycol Graft Co-Polymer[3] and PG[b] on Maltitol | 2% Polyvinyl Alcohol-Polyethylene Glycol Graft Co-Polymer "IR"[4] and PG[b] on Maltitol | 2% Eudragit RL30D[1] with PG[b] on Maltitol |
| Substrate | Maltitol | Maltitol | Maltitol | Maltitol |
| Activator | Kollicoat ® Protect | Kollicoat ® Protect | Kollicoat ® IR | Eudragit ® RL30D |
| Activator Concentration (% w/w) | 2.0 | 1.0 | 2.0 | 2.0 |
| Pharmaceutical Active Agent | N/A | N/A | N/A | N/A |
| Active Dose per tablet | N/A | N/A | N/A | N/A |
| % Lossy Coated Particles in Powder Blend | 100.0 | 100.0 | 100.0 | 100.0 |
| % Moisture of Lossy Coated Particles Before Sintering | 0.825 | 0.610 | 0.819 | 0.866 |
| e' | 1.6708 | 1.6301 | 1.6225 | 1.6786 |
| e" | 0.0217 | 0.0623 | 0.0703 | 0.0731 |
| Q value | 77 | 26 | 56 | 23 |
| Tablet Diameter (mm) | 12.5 | 12.5 | 12.5 | 12.5 |
| Tablet Weight (mg) | 600 | 600 | 600 | 600 |
| Sintering Time (sec) | 1 | 1 | 1 | 1 |
| Oral Disintegration Time (sec) | 7-10 | NR | 10 | >30 |
| Friability % (15 drops) | 1.9-2.8 | 3.9-5.8 | 2.6-6.9 | 2.9-3.8 | e' and e" tested on coated particles
a: DBS: Dibuytl Sebecate (plasticizer)
[b]PG: Propylene Glycol (plasticizer)
NR—not recorded
[3]Available as Kollicoat Protect ® from the BASF Corporation
[4]Available as Kollicoat IR ® from the BASF Corporation Example 15: Evaluation of Tablet Excipients to Prevent Sticking to Tooling During Sintering, Including the Addition of Corn Starch and Mesoporous Silica The addition of corn starch and mesoporous silica allow for anti-adherence properties and the control of moisture within the sintered ODT tablet blend, preventing the tablet from sticking to the tooling during sintering with radiofrequency energy.

Part A: Tablet Formulation Using Hydroxyethylcellulose Coated Particles with Encapsulated Acetaminophen:

Tablets were produced at a weight of 600 mg, according to the formula in Table 18. Coated maltitol was coated in a fluid bed coating unit using an aqueous solution of hydroxyethylcellulose (Example 11B) with 1% hydroxyethylcellulose, 1% glycerin and 1% sodium citrate.

The blend is then prepared using the formulation in Table 18. Encapsulated Acetaminophen, sucralose and flavoring agents were manually mixed in a plastic bag with sucralose and grape flavor until homogenous. This mixture was transferred to a Turbula blender and mixed with the Corn Starch, Syloid and coated maltitol for 5 minutes.

To produce the tablets, the blend was filled into 12.5 mm round dies and sintered at a radio frequency of 27 MHz for approximately 0.8 seconds to form an orally disintegrating tablet. Optimal levels of Corn starch and Syloid were determined through an experimental design model, using ranges of 0.625% to 2.5% Corn Starch and 0.25% to 1.0% of Syloid in varying amounts. The disintegration time as measured by USP 24 was less than 30 seconds and the friability of the tablets was 1.68, which was less than target amount of 3 percent (15 drops of 3 tablets).

TABLE 18

| Granulation Blend | % w/w | Mg/Tablet |
|---|---|---|
| Coated Maltitol Particles | 70.08 | 420.48 |
| Encapsulated Acetaminophen[1] (90% potency) | 27.90 | 167.40 |
| Grape Flavor | 0.50 | 3.00 |
| Sucralose | 0.15 | 0.90 |
| Corn Starch B830[2] | 0.625 | 3.75 |
| Syloid ® 63FP | 0.75 | 4.50 |
| TOTAL | 100.0 | 600.0 |

[1]Available from the Aptalis Corporation as Acetaminophen Microcaps ®
[2]Available from the Grain Processing Corporation
3: Available as mesoporous silica from the W.R. Grace Corporation Specific embodiments of the present invention are illustrated by way of the following examples. This invention was not confined to the specific limitations set forth in these examples.

It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A process for making a tablet comprising at least one pharmaceutically active agent, said method comprising the step of applying radiofrequency energy to a powder blend to sinter said powder blend into said tablet, wherein said powder blend comprises lossy coated particles and said at least one pharmaceutically active agent, wherein said lossy coated particles comprises a substrate that is at least partially coated with a lossy coating comprising at least one activator, wherein said substrate has a Q value of greater than 100 and said activator has a Q value of less than 75 and wherein the surface of said lossy coated particle comprises said activator wherein the friability at 15 drops of the tablet is less than about 5%.

2. A process of claim 1, wherein said activator has a Q value of less than 50.

3. A process of claim 2, wherein said substrate has a Q value of greater than 200.

4. A process of claim 1, wherein said substrate has a Q value of greater than 200.

5. A process of claim 1, wherein said lossy coated particles have a Q value of greater than 100.

6. A process of claim 1, wherein said powder blend has a Q value of greater than 100.

7. A process of claim 1, wherein said powder blend comprises at least 20%, by weight, of said lossy coated particles.

8. A process of claim 1, wherein said lossy coated particles comprise from about 0.1 to about 2%, by weight, of said at least one activator.

9. A process of claim 1, wherein said lossy coated particle comprises from about 0.1% to about 3%, by weight, water.

10. A process of claim 1, wherein said tablet disintegrates in the mouth when placed on the tongue in less than about 30 seconds.

11. The process of claim 1, wherein said radiofrequency energy has a frequency of from about 13 MHz to about 40 MHz.

12. A process of claim 1, wherein said tablets are formed within a tablet die.

13. A process of claim 1, wherein said activator is a polymer selected from the group consisting of celluloses, hydrocolloids, polymethacrylates, polyvinyls, proteins, polysaccharides, and copolymers thereof.

14. A process of claim 1, wherein said activator is hydroxypropylcellulose or hydroxyethylcellulose.

15. A process of claim 1, wherein said substrate comprises a starch, a sugar alcohol, or a sugar.

16. A process of claim 1, wherein said substrate comprises maltitol or mannitol.

17. A process of claim 1, wherein said substrate comprises said pharmaceutically active agent.

18. A process of claim 1, wherein said tablet further comprises a water scavenger.

19. A process of claim 1, wherein said tablet further comprises a plasticizer.

20. The process of claim 1 wherein said at least one pharmaceutically active agent is contained within particles separate from the lossy coated particles.

21. The process of claim 20 wherein said separate particles comprising the pharmaceutically active agent comprise a taste masking coating.

22. The process of claim 1 wherein said tablet has an in vitro disintegration time of about 30 seconds or less when based on the United States Pharmacopeia USP 24 NF29.

23. A process for making a tablet comprising the step of applying radiofrequency energy to a powder blend to sinter said powder blend into said tablet, wherein said powder blend comprises lossy coated particles and separate particles comprising at least one pharmaceutically active agent, wherein said lossy coated particles comprise a substrate that is at least partially coated with a lossy coating comprising at least one activator, wherein the Q value of the activator is less than half the Q value of the substrate wherein the friability at 15 drops of the tablet is less than about 5%.

24. The process of claim 23 wherein said tablet has an in vitro disintegration time of about 30 seconds or less when based on the United States Pharmacopeia USP 24 NF29 and the friability at 15 drops of the tablet is less than about 5%.

25. The process of claim 24 wherein said substrate comprises a sugar alcohol, or a sugar and said activator comprises a polymer selected from the group consisting of celluloses, polyvinyls, polysaccharides, and copolymers thereof.

* * * * *